US008802675B2

(12) United States Patent
Youdim et al.

(10) Patent No.: US 8,802,675 B2
(45) Date of Patent: Aug. 12, 2014

(54) NEUROPROTECTIVE MULTIFUNCTIONAL COMPOUNDS AND PHARMACEUTICAL COMPOSITIONS COMPRISING THEM

(75) Inventors: Moussa B. H. Youdim, Haifa (IL); Mati Fridkin, Rehovot (IL); Hailin Zheng, Nanning (CN)

(73) Assignees: Technion Research and Development Foundation Ltd, Haifa (IL); Yeda Research and Development Company Ltd., Rehovot (IL)

( * ) Notice: Subject to any disclaimer, the term of this patent is extended or adjusted under 35 U.S.C. 154(b) by 415 days.

(21) Appl. No.: 13/146,975

(22) PCT Filed: Jan. 31, 2010

(86) PCT No.: PCT/IL2010/000080
§ 371 (c)(1),
(2), (4) Date: Oct. 6, 2011

(87) PCT Pub. No.: WO2010/086860
PCT Pub. Date: Aug. 5, 2010

(65) Prior Publication Data
US 2012/0040993 A1 Feb. 16, 2012

Related U.S. Application Data

(60) Provisional application No. 61/148,280, filed on Jan. 29, 2009.

(51) Int. Cl.
| | | |
|---|---|---|
| A01N 43/64 | (2006.01) |
| A61K 31/53 | (2006.01) |
| A01N 43/58 | (2006.01) |
| A01N 43/60 | (2006.01) |
| A61K 31/50 | (2006.01) |
| A61K 31/495 | (2006.01) |
| A61K 31/497 | (2006.01) |
| A01N 43/54 | (2006.01) |
| A61K 31/517 | (2006.01) |
| A01N 43/42 | (2006.01) |
| A61K 31/47 | (2006.01) |
| A01N 43/40 | (2006.01) |
| A61K 31/445 | (2006.01) |
| A01N 47/10 | (2006.01) |
| A61K 31/27 | (2006.01) |
| A01N 33/02 | (2006.01) |
| A61K 31/135 | (2006.01) |
| A61K 31/13 | (2006.01) |
| C07D 253/08 | (2006.01) |
| C07D 487/00 | (2006.01) |
| C07D 239/72 | (2006.01) |
| C07D 241/36 | (2006.01) |
| C07D 401/00 | (2006.01) |
| C07D 215/16 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07C 211/00 | (2006.01) |

(52) U.S. Cl.
USPC ... 514/243; 514/249; 514/253.06; 514/266.1; 514/311; 514/659; 544/183; 544/283; 544/353; 544/363; 546/178; 546/200; 564/308; 564/336

(58) Field of Classification Search
CPC . A61K 31/133; A61K 31/27; A61K 31/4545; A61K 31/4709; A61K 31/496; A61K 31/498; A61K 31/517; A61K 31/53; A61K 31/015; C07C 13/465; C07C 13/47; C07C 15/04; C07D 211/08; C07D 215/34; C07D 239/72; C07D 241/44; C07D 247/02; C07D 253/10
USPC ......... 514/243, 249, 253.06, 266.1, 311, 323, 514/490, 649, 657, 659; 544/183, 283, 353, 544/363; 546/178, 200; 564/308, 336
See application file for complete search history.

(56) References Cited

U.S. PATENT DOCUMENTS 6,855,711 B1 2/2005 Warshawsky et al.

FOREIGN PATENT DOCUMENTS

WO WO 2004/041151 A2 5/2004

OTHER PUBLICATIONS

Sterling, et al., "Novel Dual Inhibitors of Ache and Mao Derived From Hydroxy Aminoindan and Phenethylamine as Potential Treatment for Alzheimer's Disease", Journal of Medicinal Chemistry, 2002, pp. 5260-5279, vol. 45, No. 24.
Yogev-Falach, et al., "A Multifunctional, Neuroprotective Drug, Ladostigil (TV3326), Regulates Holo-App Translation and Processing", The FASEB Journal, Oct. 2006, pp. 2177-2179, vol. 20.
Zheng, et al; "Site-Activated Multifunctional Chelator With Acetylcholinesterase and Neuroprotective-Neurorestorative Moieties for Alzheimer's Therapy", Journal of Medicinal Chemistry, Apr. 21, 2009, pp. 4095-4098, vol. 52, No. 14.

*Primary Examiner* — Sarah Pihonak
(74) *Attorney, Agent, or Firm* — Browdy and Neimark, PLLC

(57) ABSTRACT

Multifunctional compounds are provided, comprising two or more functional moieties selected from: (i) a moiety that imparts an iron chelator function; (ii) a moiety that imparts a neuroprotective function; (iii) a moiety that imparts combined antiapoptotic, neuroprotective and/or neurorestorative functions; (iv) a moiety that imparts brain MAO inhibition, preferably with little or no MAO inhibition in liver and small intestine; (v) a moiety that imparts cholinesterase inhibitory function; and (vi) a moiety that imparts an N-methyl-D-aspartic acid receptor (NMDAR) inhibition, and pharmaceutically acceptable salts and optical isomers thereof. The multifunctional compounds are useful in the treatment or prevention of diseases, disorders or conditions that can be prevented and/or treated by iron chelation therapy, and/or neuroprotection and/or neurorestoration, and/or apoptosis inhibition and/or MAO inhibition and/or cholinesterase inhibition and/or NMADR inhibition. The present invention encompasses compounds of the formulas I to VI.
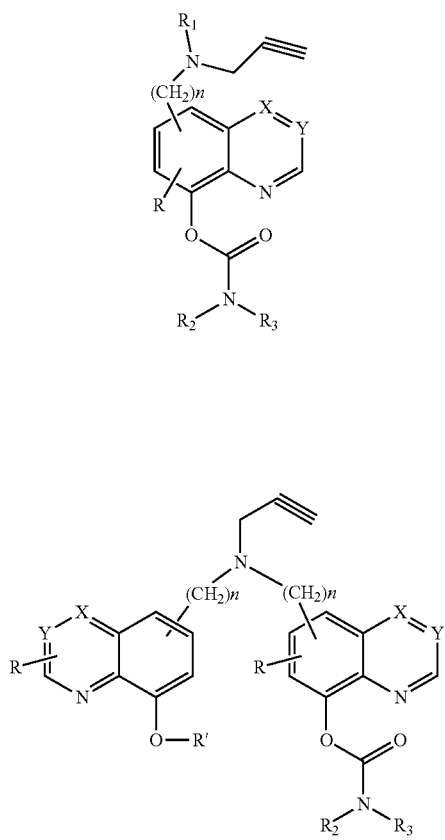
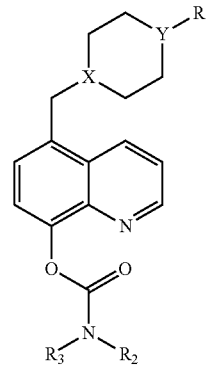
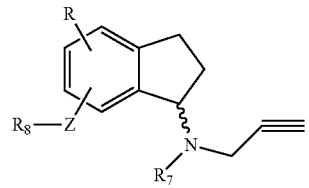
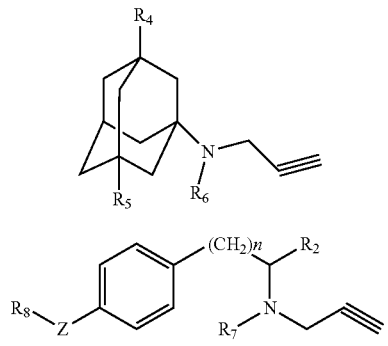
18 Claims, 15 Drawing Sheets

NEUROPROTECTIVE MULTIFUNCTIONAL COMPOUNDS AND PHARMACEUTICAL COMPOSITIONS COMPRISING THEM

FIELD OF THE INVENTION

The present invention relates to multifunctional compounds useful in the prevention and/or treatment of diseases, disorders and conditions by iron chelation therapy, and/or brain MAO inhibition, and/or apoptosis inhibition, and/or neuroprotection or neurorestoration, and/or cholinesterase inhibition and/or NMDA receptors inhibition.

BACKGROUND ART

Neuronal death in specific regions of the brain characterizes age-related neuronal degeneration and neurodegenerative conditions. Neurodegenerative diseases, such as Parkinson's disease (PD) and Alzheimer's disease (AD), are neurodegenerative syndromes for which at present no cure is available. Both diseases are the most widespread neurodegenerative disorders and affect approximately 0.5% and 4-8%, respectively, of the population over the age of 50 years, forming an increasing economic burden for society.

Numerous in vitro and in vivo studies have shown a linkage between free radical production and neurodegenerative diseases and disorders, such as PD, AD and stroke as well as ALS, multiple sclerosis, Friedreich's ataxia, Hallervorden-Spatz disease, epilepsy and neurotrauma and neurodegeneration with brain iron accumulation (NBIA) disease.

Iron accumulation and oxidative stress associated therewith have been related to a number of diseases, disorders and conditions because humans have no physiologic means of eliminating excess iron.

Iron accumulation and deposition of significant amounts of iron at the neurodegenerative sites are common features in neurodegenerative diseases, and ones of the profound aspects thereof. Iron has a pivotal role in the process of neurodegeneration (AMD) (Youdim et al, 1988) as well as age related macular degeneration (Hahn P, Milam A H, Dunaief J L, 2003). Maculas affected by age-related macular degeneration contain increased chelatable iron in the retinal pigment epithelium.

The etiology of Alzheimer's disease (AD) and the mechanism of cholinergic neuron degeneration remain elusive. In AD, iron accumulates within the microglia and within the neurons and in plaques and tangles. Current reports have provided evidence that the pathogenesis of AD is linked to the characteristic neocortical beta-amyloid deposition, which may be mediated by abnormal interaction with metals such as iron. Indeed, iron is thought to cause aggregation of not only beta-amyloid protein but also of alpha-synuclein, promoting a greater neurotoxicity. This has led to the notion that chelatable free iron may have a pivotal role in induction of the oxidative stress and inflammatory process leading to apoptosis of neurons. Iron and radical oxygen species (ROS) activate the proinflammatory transcription factor, NFκB, which is thought to be responsible for promotion of the cytotoxic proinflammatory cytokines IL-1, IL-6 and TNF-alpha, which increase in AD brains is one feature of AD pathology. This is considered logical since iron, as a transition metal, participates in Fenton chemistry with hydrogen peroxide to generate the most reactive of all radical oxygen species, reactive hydroxyl radical. This radical has been shown to be associated with protein denaturation, enzyme inactivation, and DNA damage, resulting in lipid peroxidation of cell membranes and subsequent harmful oxidative chain reactions. Such reactions cause damage to the cellular components of cells, particularly mitochondrial membranes, and therefore destroy neurons. Hydroxyl radical has been also implicated in the mechanism of action of numerous toxins and neurotoxins (6-hydroxydopamine, MPTP, kainite, streptocozin model of AD). Furthermore, such toxins mimic many of the pathologies of neurodegenerative diseases (AD, Parkinson's disease and Huntington's Chorea), one feature of which is the accumulation of iron, but not of other metals, at the site of neurodegeneration.

In Parkinson's disease, the brain defensive mechanisms against the formation of oxygen free radicals are defective. Iron concentrations are significantly elevated in Parkinsonian substantia nigra pars compacta and within the melanized dopamine neurons, wherein at the same time the activities of antioxidant enzymes at these parts of the brain are reduced. Significant accumulations of iron in white matter tracts and neurons throughout the brain, especially in the substantia nigra pars compacta, precede the onset of neurodegeneration and movement disorder symptoms.

Some of the chemical pathology of PD and AD show similarity. Apart from the involvement of increased iron, the main common features include onset of oxidative stress, loss of tissue reduced glutathione (GSH), an essential factor for removal of hydrogen peroxide, increased lipid peroxidation, the progressive nature of the disease, proliferation of reactive microglia around and on top of the dying neurons, and inflammatory processes.

Iron alone or iron decompartmentalized from its binding site by a neurotoxin, e.g. the dopaminergic neurotoxin 6-hydroxydopamine (6-OHDA), may induce oxidative stress and neurodegeneration, as evidenced in previous studies of the inventors in which intranigral administration of iron-induced "Parkinsonism" in rats and the iron chelator desferrioxamine protected the rats against 6-OHDA-induced lesions of nigrostrial dopamine neurons (Ben-Shachar et al., 1991).

The accumulation of iron at the site of neurodegeneration is one of the mysteries of neurodegenerative diseases because iron does not cross the blood-brain barrier (BBB). Where the iron comes from and why it accumulates is not known.

It has thus been suggested that treatment or retardation of the process of dopaminergic neurodegeneration in the substantia nigra may be affected by iron chelators capable of crossing the BBB. The development of iron chelators as therapeutic agents for AD and PD, as well as for treatment of age related macular degeneration has been previously suggested (Gassen and Youdim, 1999; Cuajungco et al., 2000; Sayre et al., 2000). This therapeutic approach for the treatment of PD can be applied to other metal-associated neurological disorders such as tardive dyskinesia, AD and HBIA.

Iron chelators and radical scavengers have been shown to have potent neuroprotective activity in animal models of neurodegeneration. However, the major problem with such compounds is that they do not cross the BBB. The prototype iron chelator Desferal (desferrioxamine) was first shown by M. Youdim to be a highly potent neuroprotective agent in animal models of Parkinson's disease (Ben-Schachar et al., 1991). However, Desferal does not cross the BBB and has to be injected centrally. Desferal also protects against streptozocin model of diabetes.

Stroke, the third leading cause of death in the Western world today, exceeded only by heart diseases and cancer, is characterized by a sudden appearance of neurological disorders such as paralysis of limbs, speech and memory disorders, sight and hearing defects, etc., which result from a cerebrovascular damage.

Hemorrhage and ischemia are the two major causes of stroke. The impairment of normal blood supply to the brain is associated with a rapid damage to normal cell metabolism including impaired respiration and energy metabolism lact-acidosis, impaired cellular calcium homeostasis, release of excitatory neurotransmitters, elevated oxidative stress, formation of free radicals, etc. Ultimately these events lead to cerebral cell death and neurological dysfunction.

Vascular damage associated with stroke relates to elevated oxidative stress, which is caused by free radical formation and iron chelators could prevent much of the damages caused by local ischemia. Indeed, the known free radical scavengers lazaroides (21-amino steroids) have shown significant improvement of local and global ischemia damages in vivo.

Iron accumulation in aging and the resulting oxidative stress has been suggested to be a potential causal factor in aging and age-related neurodegenerative disorders (Butterfield et al., 2001). Iron chelators have thus been suggested to favor successful ageing in general, and when applied topically, successful skin ageing (Polla et al., 2003). Iron is a factor in extrinsic type of skin ageing termed photo-ageing and in non-age related skin photodamage, apparently by way of its participation in oxygen radical production. UVA radiation-induced oxidative damage to lipids and proteins in skin fibroblasts was shown to be dependent on iron and singlet oxygen. Iron chelators can thus be used in cosmetic and non-cosmetic formulations, optionally with sunscreen compositions, to provide protection against UV radiation exposure. Certain topical iron chelators were found to be photoprotective (Bisset and McBride, 1996; Kitazawa et al., 1999).

Other diseases, disorders or conditions associated with iron overload include: (i) viral infections, including HIV infection and AIDS where oxidative stress and iron have been described to be important in the activation of HIV-1. Iron chelation, in combination with antivirals, might add to improve the treatment of viral, particularly HIV disease (van Asbeck et al., 2001); (ii) protozoal, e.g. malaria, infections; (iii) yeast, e.g. *Candida albicans*, infections; (iv) cancer where several iron chelators have been shown to exhibit anti-tumor activity and may be used for cancer therapy either alone or in combination with other anti-cancer therapies (Buss et al., 2003); (v) iron chelators may prevent cardiotoxicity induced by anthracycline neoplastic drugs (Hershko et al., 1996); (vi) inflammatory disorders where iron and oxidative stress have been shown to be associated with inflammatory joint diseases such as rheumatoid arthritis (Andrews et al., 1987; Hewitt et al., 1989; Ostrakhovitch et al., 2001); (vii) diabetes where iron chelators have been shown to delay diabetes in diabetic model rats (Roza et al., 1994); (viii) iron chelators have been described to be potential candidates for treatment of cardiovascular diseases, e.g. to prevent the damage associated with free radical generation in reperfusion injury (Hershko, 1994; Flaherty et al., 1991); (ix) hereditary hemochromatosis and thalassemias that are currently treated with the orally-active drug deferasirox; and (x) iron chelators may be useful ex-vivo for preservation of organs intended for transplantation such as heart, lung or kidney (Hershko, 1994).

Neuronal degeneration in the CNS, particularly in the dopamine system, may be caused by an increase in oxidative stress derived from monoamine oxydase (MAO)-catalyzed oxidative deamination of dopamine and other amines. In these reactions, hydrogen peroxide is produced as a side product. In the presence of transition metal ions such as iron and copper, hydrogen peroxide is converted to hydroxyl free radical.

Brain monoamine oxidases A (MAO-A) and B (MAO-B) are two isoforms of the enzyme proven to be important drug targets for treatment of neurodegenerative and central nervous system disorders. The isoform MAO-A preferentially deaminates serotonin, melatonin, epinephrine and norepinephrine. MAO-B preferentially deaminates phenylethylamine and trace amines. Dopamine is equally deaminated by both isoforms. Monoamine oxydase inhibitors (MAOIs) act by inhibiting the activity of monoamine oxidase, thereby preventing the breakdown of monoamine neurotransmitters, and increasing their availability. Hence, selective MAO-A and MAO-B inhibitors are good candidates for use as antidepressants, for treating depression associated with various neurodegenerative diseases, for use as anti Parkinson drugs and for treatment of the causes of various neurodegenerative diseases. Several MAO inhibitors have been approved for treatment of depression and neurodegenerative diseases. For example, the MAO inhibitor rasagiline is approved for treatment of PD in several European countries and the United States. Selegiline, a selective inhibitor of MAO-B is used in the treatment of PD and has been shown to postpone the need for levodopa and spairing levodopa in early PD. However, these MAOI exhibit side effects as a result of inhibiting the catabolism of dietary amines. Sufficient intestinal MAO-A inhibition can lead to hypertensive crisis when foods containing tyramine are consumed (so-called "cheese syndrome"), or hyperserotonemia if foods containing tryptophan are consumed. The extant of side reaction varies among individuals and depends on the degree of MAO inhibition, and dosage and selectivity of the MAOIs used.

In patients with AD there is a relative shortage of the neurotransmitter acetylcholine, which is important in the ability to form new memories. Cholinesterase inhibitors (ChEIs) block the breakdown of acetylcholine, and this results in increased availability of acetylcholine in the brain and, most probably, formation of new memories. Four ChEIs have been approved by the FDA and three of them, donepezil hydrochloride, rivastigmine and galantamine are used by most physicians. There is no significant difference between these three drugs in their effectiveness in treating Alzheimer's disease, while the fourth drug, tacrine, has more undesirable side effects than the other three. Rivastigmine and galantamine are approved by the FDA only for mild to moderate Alzheimer's disease, whereas donepezil is approved for mild, moderate, and severe Alzheimer's disease. Several studied suggest that the progression of symptoms in patients treated with any one of these drugs plateau for six to twelve months, and then progression of the disease continues.

Apoptosis is considered by many experts to be an important contributor in various neurodegenerative diseases, and anti apoptotic drugs may slow down the progression of such diseases. The brains of Alzheimer's patients contain dying neurons that display some characteristic signs of apoptosis, such as DNA breaks and activation of caspases that carry out the death program. This finding leads to highly desirable new therapy strategies. N-propargylamine in known to confers its antiapoptopic activity via multiple neuroprotective pathways.

The N-methyl-D-aspartic acid (NMDA) class of glutamate receptors (NMDARs) plays a critical role in the CNS by conferring synaptic plasticity, axonal sprouting, growth, and migration. Activation of NMDARs results in the opening of an ion channel that is nonselective to cations. This allows flow of $Na^+$ and small amounts of $Ca^{2+}$ ions into the cell and $K^+$ out of the cell. Calcium flux through NMDARs action is thought to play a critical role in synaptic plasticity, a cellular mechanism for learning and memory.

High levels of neurotransmitter glutamate and of the synthetic excitotoxin NMDA (an agonist of NMDARs) overactivate NMDARs and cause a pathological process by which nerve cells are damaged and killed. Excitotoxicity occurs by increasing $Ca^{2+}$ influx into cells, resulting in activation of a number of enzymes, which damage cell structures such as components of the cytoskeleton, membrane, and DNA. Excitotoxicity may be involved in spinal cord injury, stroke, traumatic brain injury and neurodegenerative diseases of the CNS such as Multiple sclerosis, AD, Amyotrophic lateral sclerosis (ALS), PD, Alcoholism and Huntington's disease.

Adamantane and derivatives thereof are known to block the channels of NMDA receptors by acting as antagonists (see, for example, Sobolevsky and Koshelev 1998; Antonov, 1995).

Drugs with the brain as the site of action should, in general, be able to cross BBB in order to attain maximal in vivo biological activity. However, one of the main problems in the use of chelating agents as antioxidant-type drugs is their limited transport through cell membranes or other biological barriers. The efficacy of the best established iron-chelating drug, Desferal, in neurodegenerative diseases, is limited by its ineffective transport property and high cerebro- and oculo-toxicity.

For this reason, 8-hydroxyquinolines and hydroxypyridinones have been proposed for iron binding as antioxidant-type drugs. 8-Hydroxyquinoline is a strong chelating agent for iron, and contains two aromatic rings, which can scavenge free radicals by themselves. In U.S. Pat. No. 6,855,711, various iron chelators have been disclosed and their action in Parkinson's disease prevention has been shown. The lead compound, 5-[4-(2-hydroxyethyl)piperazin-1-ylmethyl]-8-hydroxyquinoline, was able to cross the BBB and was shown to be active against 6-hydroxydopamine (6-OHDA) in an animal model of PD.

In PCT Publication No. WO 2004/041151 A2, various iron chelators and multifunctional compounds have been disclosed and their action in Parkinson's disease prevention has been shown. The lead compound M30 was able to cross the BBB and was shown to be active against 6-OHDA in an animal model of PD.

Dual inhibitors of AChE and MAO derived from hydroxy aminoindane and phenethylamine as potential treatment for Alzheimer's disease are disclosed in Sterling et al. 2002. Carbamate derivatives of N-propargylaminoindans and N-propargylphenethylamines were designed to combine inhibition of both AChE and MAO by virtue of their carbamoyl and propargylamine pharmacophores.

Yogev-Falach et al. (Yogev-Falach et al., 2006) disclose the bifunctional drug ladostigil (TV3326) [(N-propargyl-(3R) aminoindan-5-yl)-ethyl methyl carbamate], which combines the neuroprotective effects of the antiparkinson drug rasagiline with the ChE inhibitory activity of rivastigmine in a single molecule, as a potential treatment for AD and Lewy Body disease.

It is highly desirable to develop multifunctional neuroprotective and/or neurotherapeutic compounds as drug candidates that would posses combined functions of iron chelation, inhibition of apoptosis, inhibition of brain monoamine oxidases A and B, and/or inhibition of cholinesterase, that would also exhibit good transport properties through cell membranes, particularly, the blood brain barrier, as well as optimal oral uptake and optimal or sufficient pharmacokinetic behavior.

SUMMARY OF INVENTION

In a main aspect of the present invention, multifunctional compound are provided, comprising at least two functional moieties selected from: (i) a moiety that imparts an iron chelator function; (ii) a moiety that imparts a neuroprotective function; (iii) a moiety that imparts combined antiapoptotic, neuroprotective and neurorestorative functions; (iv) a moiety that imparts brain MAO inhibition, preferably with little or no MAO inhibition in liver and small intestine; (v) a moiety that imparts cholinesterase inhibitory function; and (vi) a moiety that imparts an N-methyl-D-aspartic acid receptor (NMDAR) inhibition, and pharmaceutically acceptable salts and optical isomers thereof, provided that when the compound has a sole moiety conferring iron chelation function, one or more moieties that imparts neuroprotective function, and/or one or more moieties that imparts combined antiapoptotic and neuroprotective functions, the iron chelator function is not a moiety of 8-hydroxy-5-quinolinylmethylene, 3-hydroxypyridin-4-one or 1-hydroxypyridin-2-one or the hydroxamate moiety CONHOH—$(CH_2)_2$—.

In certain embodiments, the multifunctional compounds of the invention may contain one or more of the following functional moieties: (i) as the iron chelator a hydroxamate moiety, a N-hydroxy carbamate moiety, a N-alkyl-N-hydroxy carbamate moiety, a 8-hydroxyquiniline moiety, a 8-hydroxy-1,4-benzodiazine moiety, a 8-hydroxy-1,3-benzodiazine moiety, a 3-hydroxypyridin-4-one moiety or a 1-hydroxypyridin-2-one moiety; (ii) as the moiety that imparts a neuroprotective function to the compound, a neuroprotective peptide, a neuroprotective peptide fragment and an analog thereof, in which one amino acid residue is replaced by a L- or D-cysteine residue; (iii) as the moiety imparting combined antiapoptotic, neuroprotective and/or neurorestorative functions, a propargyl amine group; (iv) as the moiety that imparts brain MAO inhibition function, a propargyl amine group, preferably linked to an aminoindane moiety or to a phenethylamine moiety; (v) as the moiety that imparts cholinesterase inhibitory function, a carbamoyl moiety; and (vi) as the moiety that imparts NMDAR inhibition, an adamantyl radical.

In certain embodiments, the multifunctional compounds of the invention contain one or more masked or latent functional moieties, more preferably one or more latent pharmacophore for chelating metal ions, selected from a quinoline, 1,4-benzodiazine or 1,3-benzodiazine moiety that have no free hydroxy group in position 8, a pyridin-4-one moiety that has no free hydroxyl moiety at position 3 or a pyridin-2-one moiety that has no free hydroxyl moiety at position 1. These latent functional moieties are masked or protected, preferably via binding to another functional moiety, and becomes active only at the target site following removal of the protecting/masking (functional) moiety.

In certain embodiments, the multifunctional compounds of the invention are the compounds of the formulae I to VI herein, particularly the compounds presented in Table 1.

In another aspect, the invention provides pharmaceutical compositions comprising the multifunctional compounds and a pharmaceutically acceptable carrier.

In a further aspect, the present invention relates to a method for preventing and/or treating conditions, disorders or diseases that can be prevented and/or treated by iron chelation therapy, and/or neuroprotective and neurorestorative therapies, and/or antiapoptotic therapy, and/or MAO inhibition, and/or cholinesterase inhibition, and/or NMDA receptor inhibition, said method comprises administering to an individual in need thereof an effective amount of a compound of the invention or a pharmaceutical composition comprising same.

The diseases, disorders and conditions which can be treated according to the invention include neurodegenerative or cerebrovascular diseases such as Parkinson's disease, Alzheimer's disease, Huntington's disease, stroke and amyotrophic lateral sclerosis; thalassemia; a cardiovascular disease; diabetes; an inflammatory disorder; a viral infection such as a retroviral infection; a protozoal infection; a yeast infection; retarding ageing by prevention of ageing-related diseases; ophthalmic disease including age related macular degeneration and glaucoma; prevention and/or treatment of skin ageing and skin protection against sunlight and/or UV light; and various severities of depressions, including depression associated with another disease or condition such as Parkinson's disease, Alzheimer's disease and vascular dementia.

In still another aspect, the present invention provides the use of the compounds of the invention, or pharmaceutically acceptable salts thereof or optical isomers thereof for preventing and/or treating conditions, disorders or diseases that can be prevented and/or treated by iron chelation therapy, and/or neuroprotection and/or neurorestoration, and/or apoptosis inhibition, and/or MAO inhibition, and/or cholinesterase inhibition, and/or NMDA receptor inhibition.

In yet another aspect, the invention provides processes for the preparation of multifunctional compounds of the invention.

BRIEF DESCRIPTION DRAWINGS

FIGS. 1A-1B are absorption spectra of M30 and compound 13 in the absence and presence of various metal salts. 1A: (a) M30; (b) M30+ZnCl$_2$; (c) M30+CuSO$_4$; (d) M30+FeCl$_3$; and (e) M30+FeSO$_4$. 1B: (a) compound 13; (b) compound 13+ZnCl$_2$; (c) compound 13+CuSO$_4$; (d) compound 13+FeSO$_4$; and (e) compound 13+FeCl$_3$.

FIGS. 2A-2B are absorption spectra of HLA20 and compound 23 in the absence and presence of various metal salts. 2A: (a) HLA20, (b) HLA20+ZnCl$_2$, (c) HLA20+CuSO$_4$, (d) HLA20+FeSO$_4$, (e) HLA20+FeCl$_3$. 2B: (a) compound 23; (b) compound 23+ZnCl$_2$; (c) compound 23+CuSO$_4$; (d) compound 23+FeSO$_4$; and (e) compound 23+FeCl$_3$.

Figure 5A:
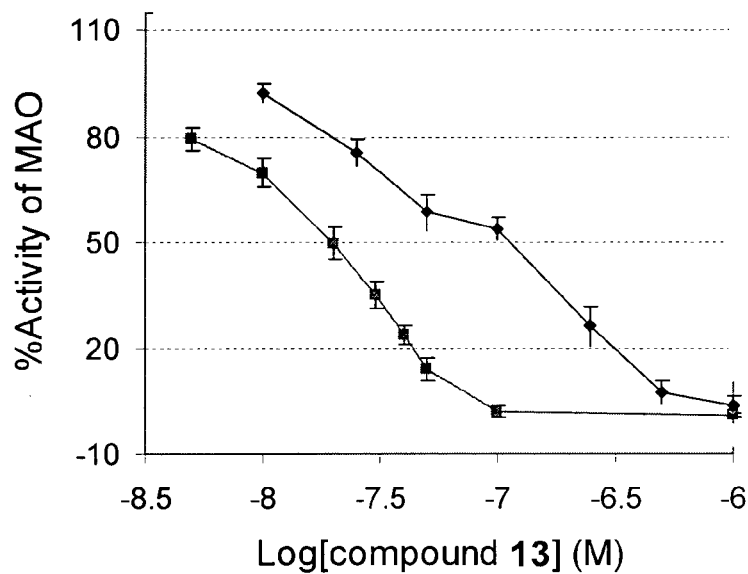
Figure 5B:
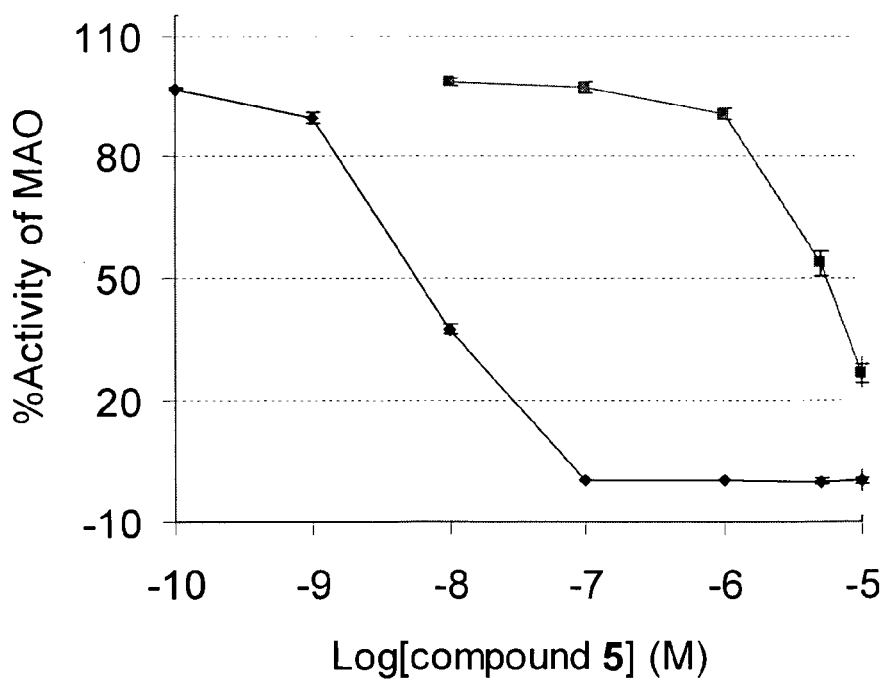
Figure 5C:
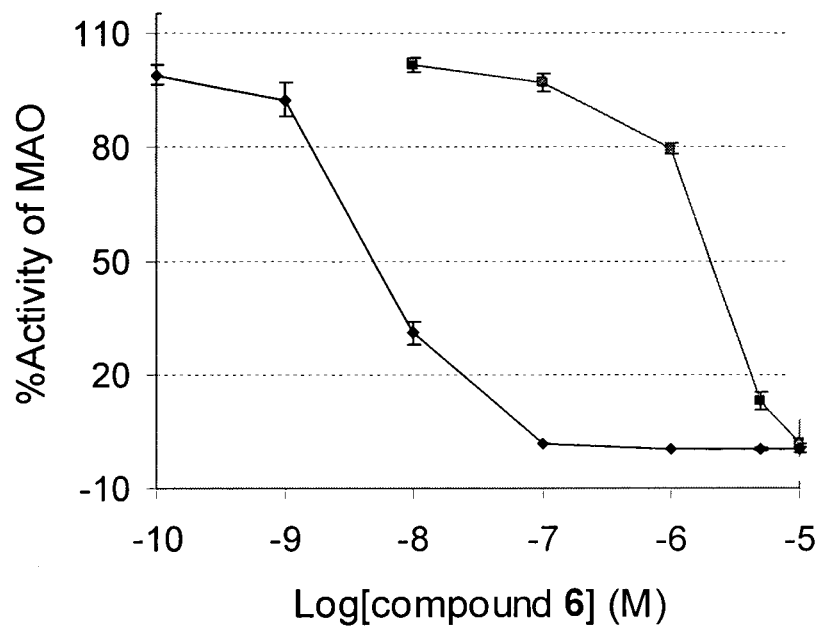
Figure 6A:
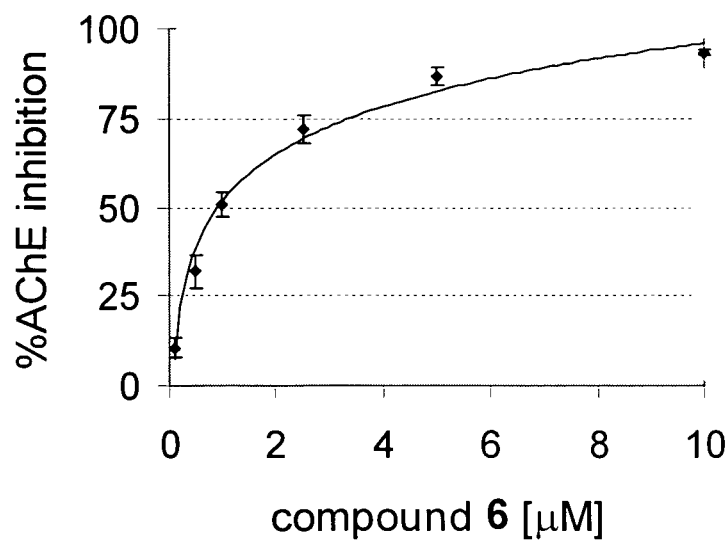
Figure 6B:
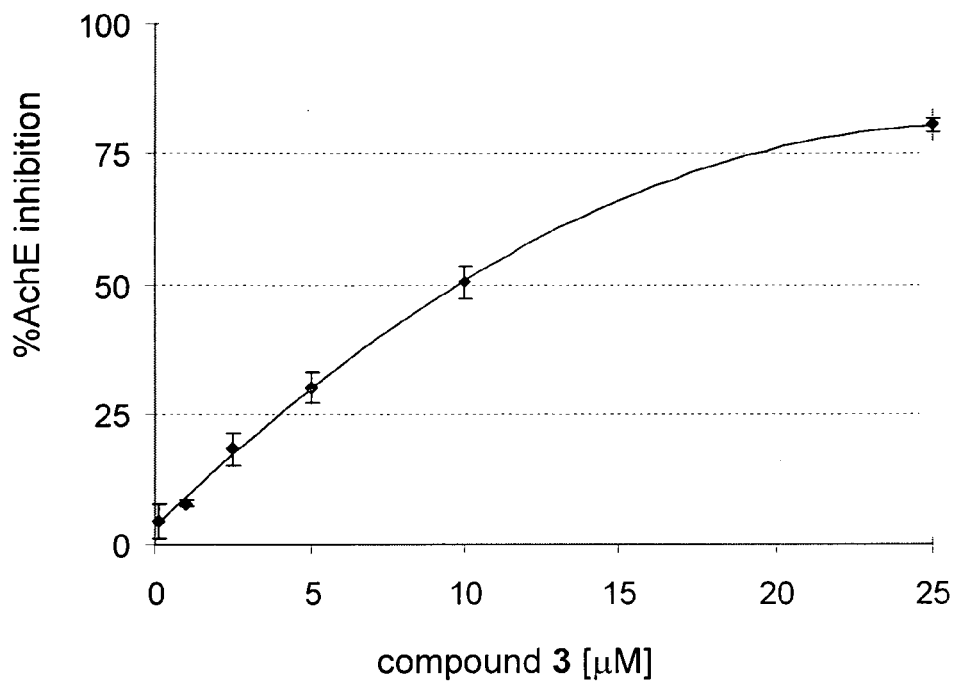
Figure 6C:
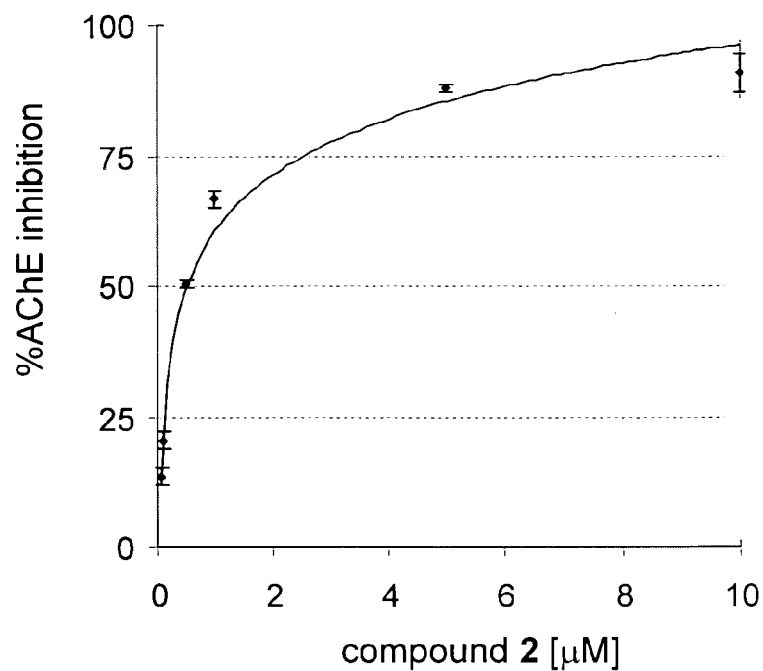
Figure 6D:
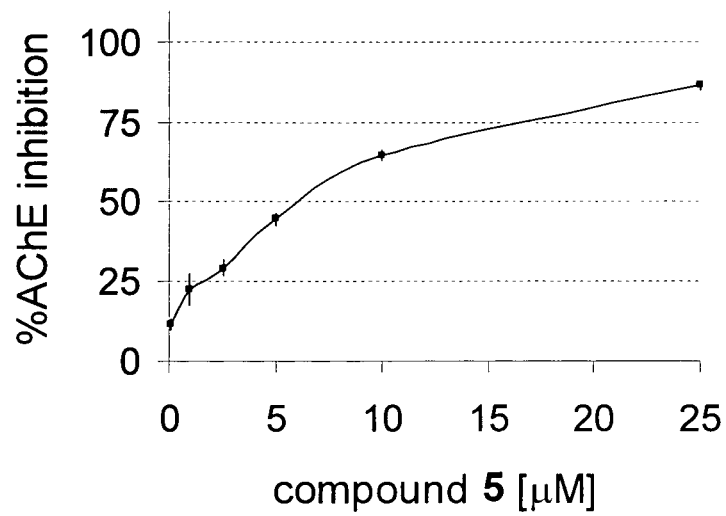
Figure 6E:
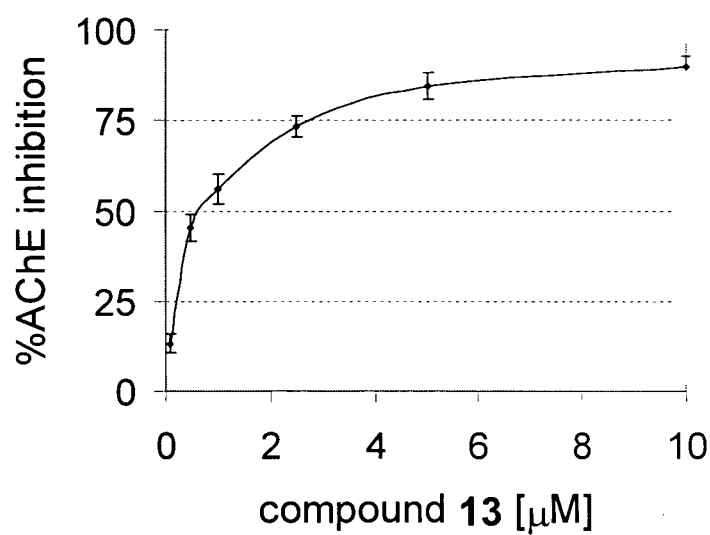
Figure 6F:
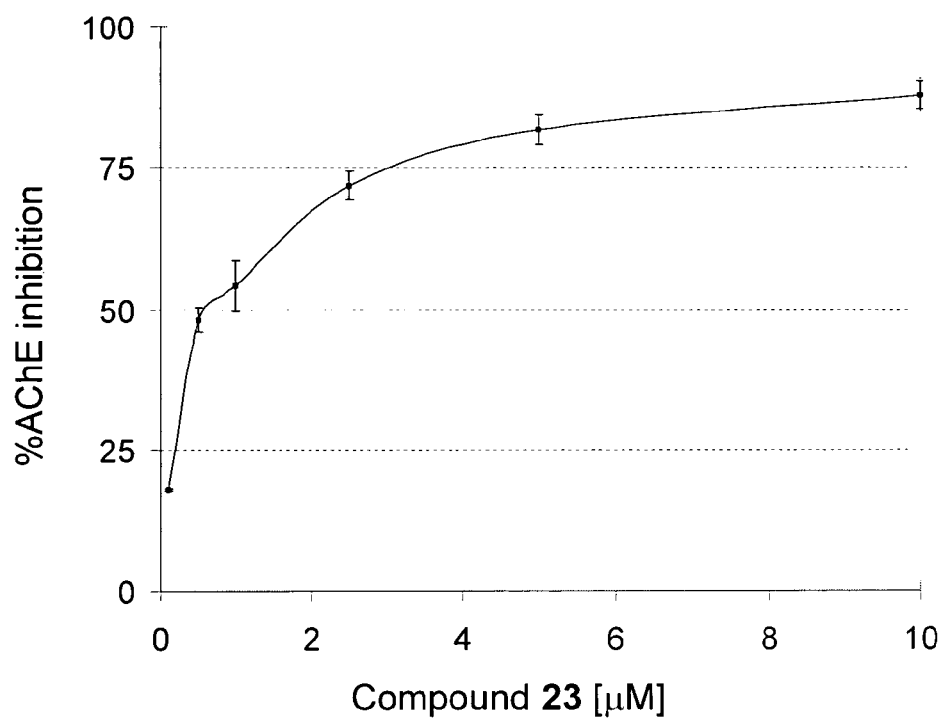
Figure 7A:
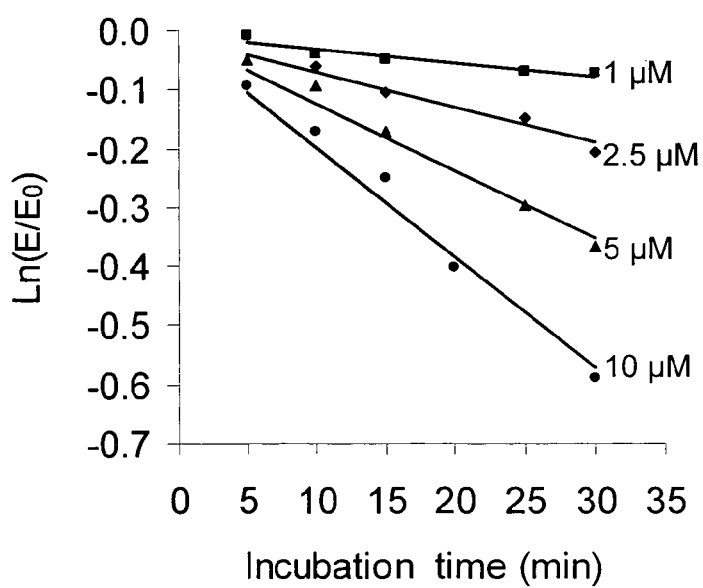
Figure 7B:
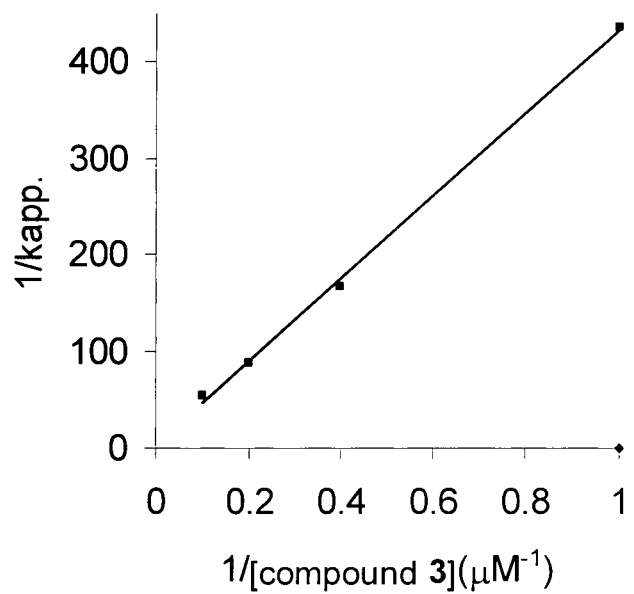
Figure 7C:
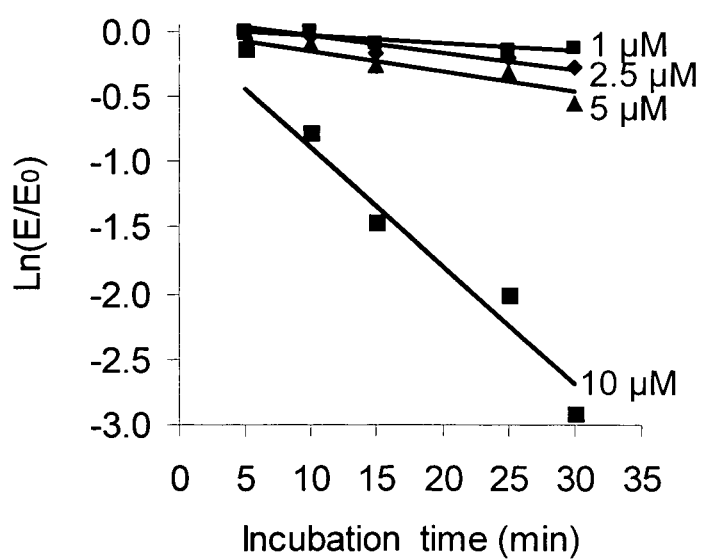
Figure 7D:
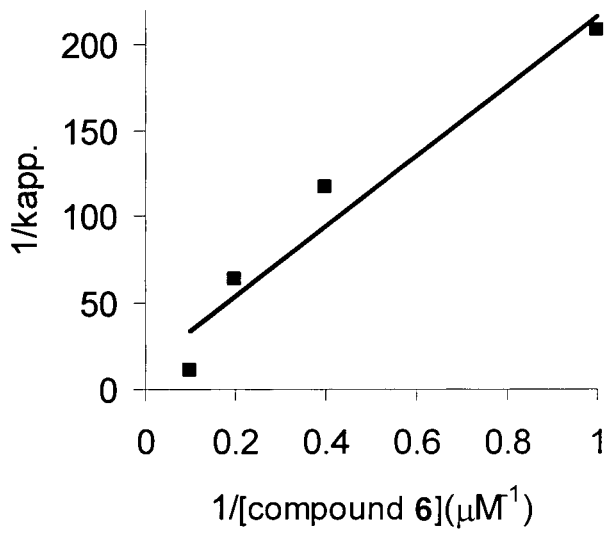
Figure 7E:
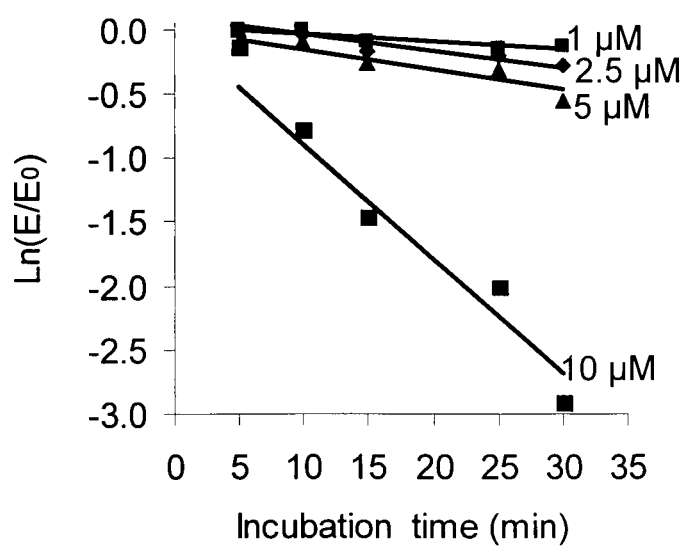
Figure 7F:
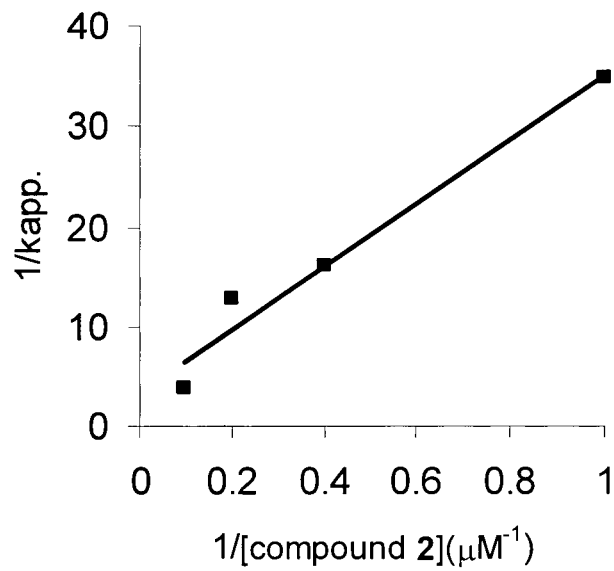
Figure 7G:
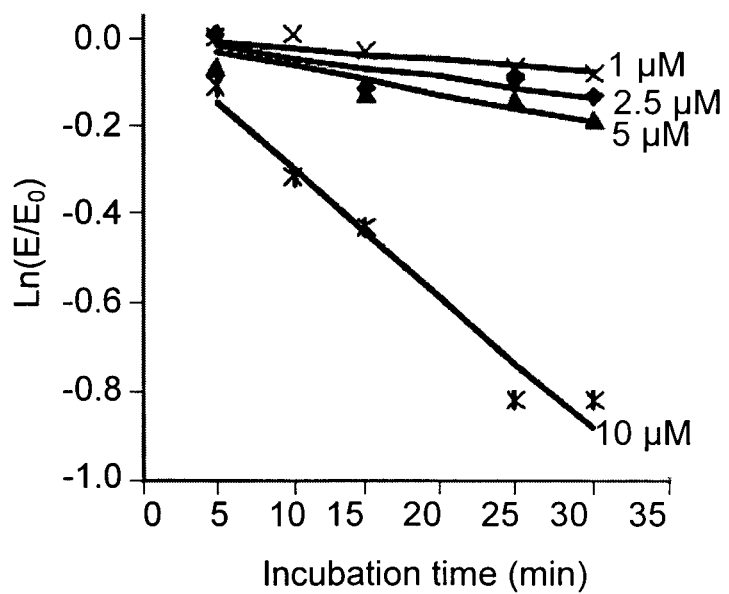
Figure 7H:
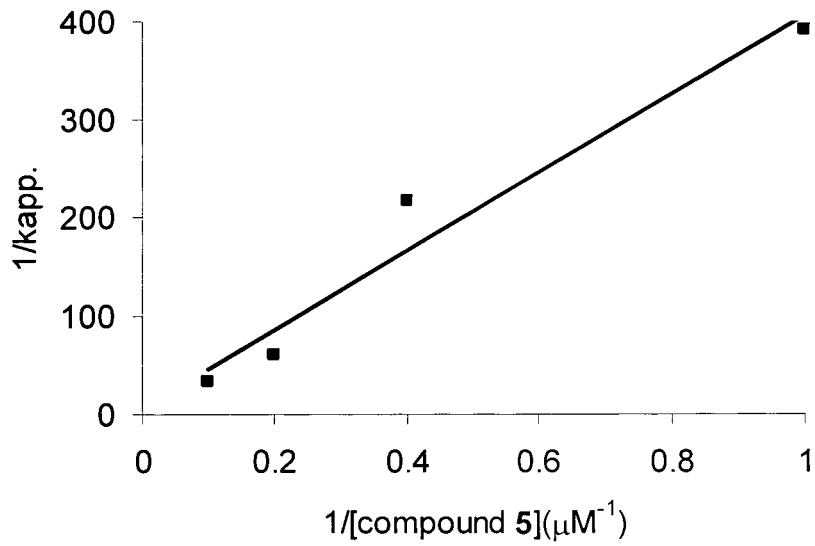
Figure 7I:
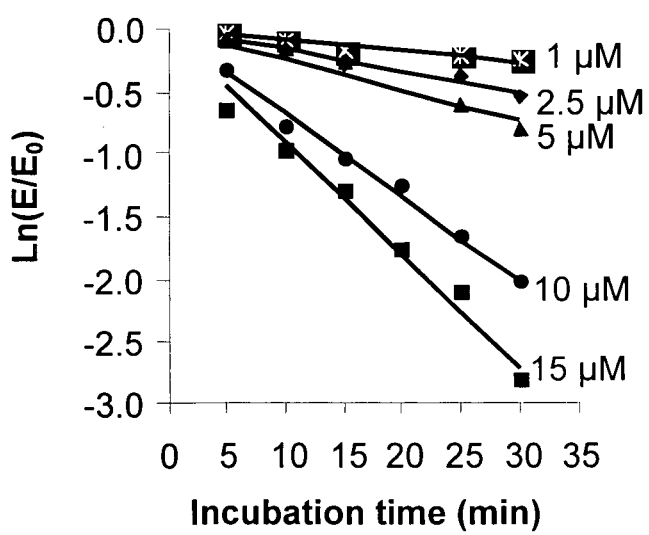
Figure 7J:
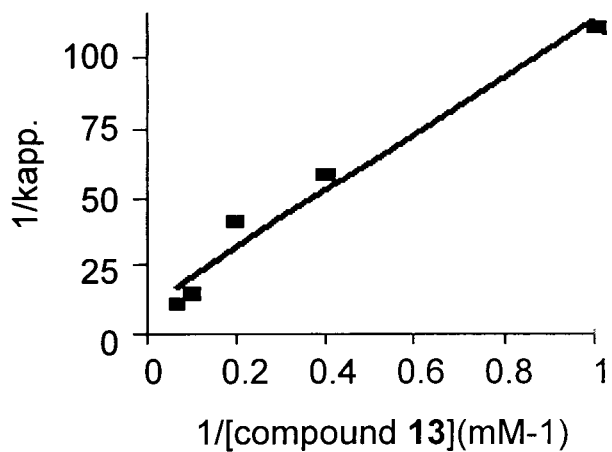
Figure 7K:
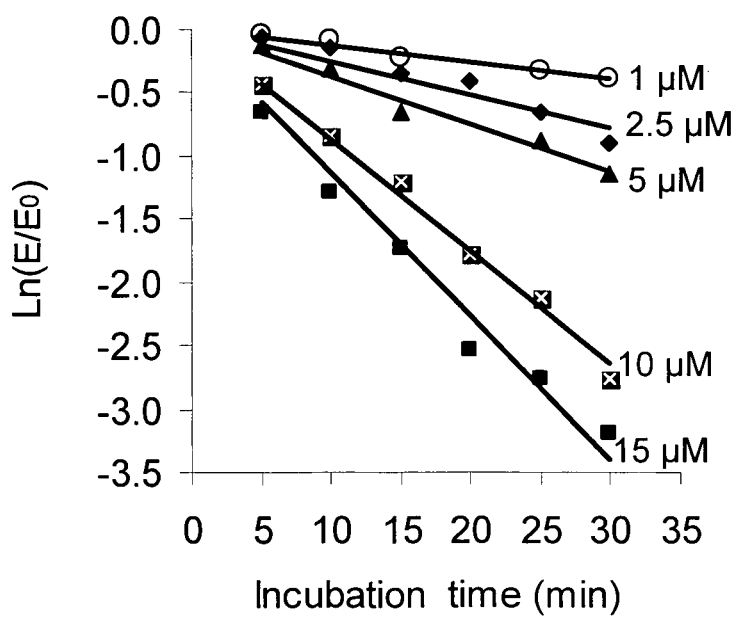
Figure 7L:
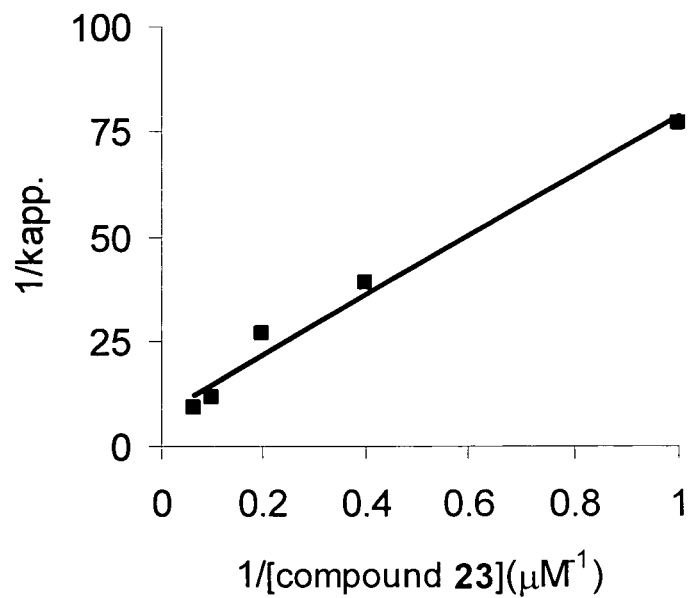

FIGS. 5A-5C are graphs showing the in vitro inhibition of rat brain MAO-A and MAO-B by compound 13 (5A, MAO-A (■), MAO-B (♦)), compound 5 (5B, MAO-A (♦), MAO-B (■)) and compound 6 (5C, MAO-A (♦), MAO-B (■)). The results are the mean SEM, n=3 in triplicates.

FIGS. 6A-6F are graphs showing the concentration-dependent inhibition of total ChE in rat brain homogenates by compound 6 (6A), compound 3 (6B), compound 2 (6C), compound 5 (6D) and compound 13 (6E), and of compound 23 (6F). Each value shows the mean with the SEM of four different experiments each done in triplicate.

FIGS. 7A-7L are graphs showing the kinetics of inhibition of rat brain cholinesterase (total ChE) with compound 3, compound 6, compound 2, compound 5, compound 13 and compound 23. 7A, 7C, 7E, 7G, 7I and 7K show time and concentration-dependent inhibition of total ChE, and 7B, 7D, 7F, 7H, 7J and 7L are Kitz-Wilson plots of the double reciprocal of the pseudo-first-order inhibition rate constant (kapp) determined from linear regression as a function of inhibitor concentration.

Figure 8A:
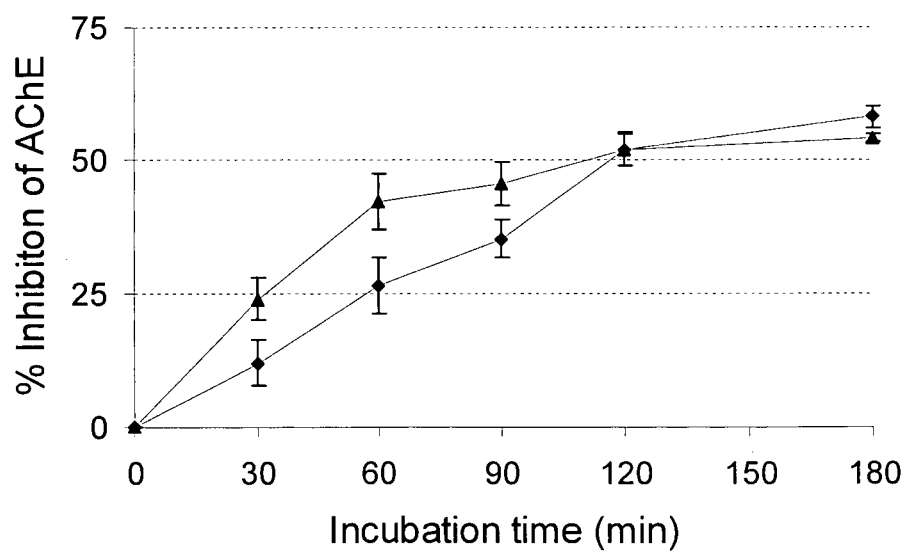
Figure 8B:
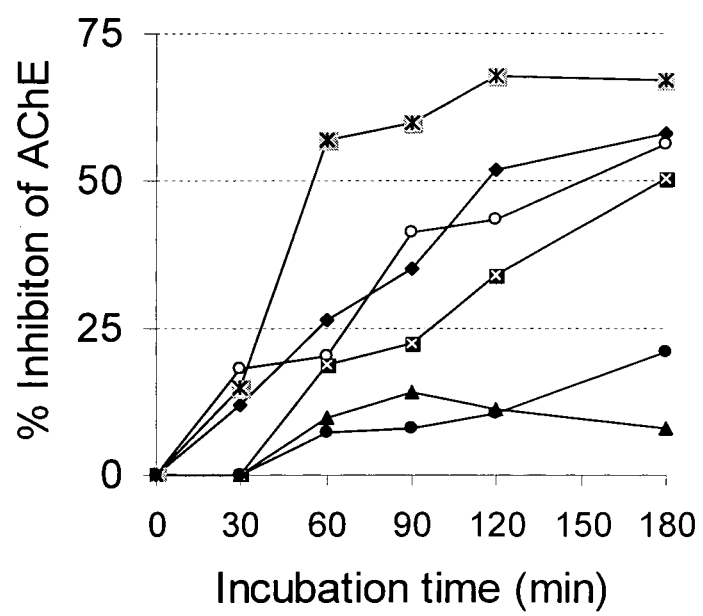

FIGS. 8A-8B are show the time courses of total ChE inhibition for compound 23 (▲) and Rivastigmine (♦) (8A), and for compound 2 (■), compound 13 (○), compound 6 (☒), compound 5 (•) and compound 3 (▲) as compared to rivastigmine (♦)(8B).

MODES OF CARRYING THE INVENTION

In one broad aspect, the present invention provides a multifunctional compound comprising two or more functional moieties selected from: (i) a moiety that imparts an iron chelator function; (ii) a moiety that imparts a neuroprotective function; (iii) a moiety that imparts combined antiapoptotic, neuroprotective and/or neurorestorative functions; (iv) a moiety that imparts brain MAO inhibition, preferably with little or no MAO inhibition in liver and small intestine; (v) a moiety that imparts cholinesterase inhibitory function; and (vi) a moiety that imparts an N-methyl-D-aspartic acid receptor (NMDAR) inhibition, and pharmaceutically acceptable salts and optical isomers thereof, provided that when the compound has a sole moiety that imparts iron chelator function, one or more moieties that impart neuroprotective function, and/or one or more moieties that impart combined antiapoptotic and neuroprotective functions, the iron chelator function is not a moiety of 8-hydroxy-5-quinoline, 3-hydroxypyridin-4-one or 1-hydroxypyridin-2-one or the hydroxamate moiety CONHOH—(CH$_2$)$_2$—.

The multifunctional compounds of the present invention are useful in, but not limited to, the treatment of neurological diseases of the CNS, particularly various neuropsychiatric disorders in humans, such as Parkinsonism, Alzheimer's disease (AD), depression, attention deficit disorders, hyperactive disorders, and ageing as well as for improving the quality of life in humans due to the combined effect of MAO inhibition, excess iron removal, inhibition of neuron cells death, neuroprotection and neurorestoration, and/or increasing central cholinergic and/or glutamate neurotransmission.

In certain embodiments, one or more of the functional moieties are masked or protected or blocked via bonding to a masking or protecting group. Such a latent functional groups is termed herein a "pro-active moiety" or a "pro-active function". This latent function becomes unmasked and therefore fully active primarily at the target site under certain conditions.

In certain embodiments, the protecting or masking moiety is another functional moiety of the multifunctional compound. The masking functional moiety is cleaved or dissociated from the multifunctional compound upon its binding to one of its relevant targets at the target site, thereby unmasking the pro-active moiety and releasing the fully active function that facilitates binding to another relevant target.

In certain embodiments, the pro-active functions are a pro-iron chelation functions, and multifunctional compounds comprising a pro-iron chelation function are referred to as "multifunctional pro-chelators".

The present multifunctional compounds comprise two or more of the functional moieties mentioned above, in the active or pro-active form.

In certain embodiments, the multifunctional compounds of the present invention comprise five different functional moieties, for example, a moiety that imparts an iron-chelator function, a moiety that imparts neuroprotection, a moiety that imparts combined antiapoptotic, neuroprotective and/or neurorestorative functions, a moiety that imparts brain MAO inhibition, and a moiety that inhibits cholinesterase. Other multifunctional compounds of the invention comprise two moieties which impart iron chelation function, two moieties that inhibit cholinesterase and one moiety that imparts combined antiapoptotic, neuroprotective and/or neurorestorative functions.

In certain embodiments, the multifunctional compounds comprise three functional moieties. Such compounds comprise, for example, one moiety that imparts an iron-chelator function, one moiety that imparts combined antiapoptotic, neuroprotective and/or neurorestorative functions and one moiety that imparts brain MAO inhibition. Other compounds comprising three functional moieties comprise one moiety that imparts combined antiapoptotic, neuroprotective and/or neurorestorative functions, one moiety that imparts brain MAO inhibition and one moiety that inhibits NMDA receptors (i.e., functions as NMDA antagonist).

In certain additional embodiments, the compounds are bi-functional compounds comprising two functional moieties, particularly, one moiety that imparts cholinesterase inhibition and one that imparts an iron chelator function.

In certain embodiments, the moiety imparting combined antiapoptotic, neuroprotective and/or neurorestorative functions is a propargyl amine group.

MAO-B activity is known to be elevated in ageing brain. The excessive deamination observed in aging brains results in oxidative stress (caused, e.g., by $H_2O_2$). Reduction of such stress by inhibiting MAO-catalyzed deamination reactions is therefore rational as a treatment to reduce neuronal deterioration. Since the inhibition of MAO-B appears to alleviate the symptoms of aging associated diseases such as Parkinson's disease and Alzheimer's disease, suitable MAO-B inhibitors are still highly desirable, especially in view of the limited and relatively inefficient treatments available for these diseases.

Simple alkyl N-methyl-propargylamine derivatives are known to be very potent, selective and irreversible monoamine oxidase B inhibitors. In addition, a series of propargyl amines were shown in the art to suppress the apoptotic cascade, prevent collapse of mitochondrial membrane potential, activate caspase 3 and fragmentate nucleosomal DNA. Propargylamines may thus regulate the apoptotic machinery in mitochondria and rescue or protect deteriorated neurons in neurodegenerative disorders.

Rasagiline (N-propargyl-(1R)-aminoindane) is an irreversible inhibitor of monoamine oxidase used as a monotherapy in early Parkinson's disease or as an adjunct therapy in more advanced cases. It is selective for MAO type B over type A by a factor of fourteen. The chemical structure of rasagiline comprises an aminoindane moiety and a propargyl group.

Selegiline, the first MAO inhibitor approved for use in Parkinson's disease in the United States, is chemically similar to methamphetamine and contains a phenethylamine moiety linked to an N-methyl propargyl group. The aminoindan and phenethylamine groups help to improve MAOI activity and selectivity for MAO-B.

In the iron chelators disclosed in the art, particularly those disclosed in WO 2004/041151, the iron chelating function is provided by a free hydroxy group which is attached directly to the an aromatic ring. Thus, a moiety of quinoline, 1,4-benzodiazine or of 1,3-benzodiazine, which have a free hydroxy group at position 8, or of a pyridin-4-one that has free hydroxyl group at position 3, or of a pyridin-2-one that has free hydroxyl group at position 1, are functioning as iron chelators. The free hydroxy group is the key-chelating group, which confers metal chelating properties to the compounds. In addition, the free hydroxyl group may act as an antioxidant and effectively trap free radicals.

However, this key-chelating group also confers systemic toxicity to the compounds since, being a strong metal chelator, it interferes with normal metal metabolism, a common toxicity associated with chelation therapies.

Some of the multifunctional compounds of the invention, particularly those that function as cholinesterase inhibitors, are multifunctional pro-chelators and comprise one or more pro-iron chelator functions. In these compounds, the iron chelating property becomes functional only at the target site under conditions in which cholinesterase is inhibited. Such pro-chelators comprise a masked or protected hydroxyl group in position 8 of the quinoline, 1,4-benzodiazine or 1,3-benzodiazine moieties, or in position 3 of pyridin-4-one moieties, or in position 1 of pyridin-2-one moiety. In certain pro-chelators of the invention masking of the hydroxyl group is facilitated by linking the oxygen atom to a N,N-dialkylcarbamoyl moiety [N(RR')CO—], which, in turn, imparts cholinesterase inhibition activity to the compounds. Upon binding to cholinesterase (ChE) or acetyl cholinesterase (AChE) in the brain, the N,N-dialkylcarbamoyl moiety is dissociated from the multifunctional pro-chelator, thus releasing or exposing a free hydroxyl group. The pro-chelator, which loses its masks while binding and inhibiting AChE in the brain, becomes active chelator, which passivates excess cerebral metal ions and protects neuronal cells from reactive oxygen species (ROS). Since the pro-chelators of the invention do not have a free hydroxyl group attached to an aromatic ring, they would have little to no chelating affinities for metal ions, and thereby would not interfere with healthy metal metabolism in the body.

Cholinesterase inhibition function is provided to the compounds of the invention by an N,N-dialkyl carbamoyl moiety N(RR')—C(O)—, wherein R and R' are H or hydrocarbyl.

It has long been known that exposure to cholinesterase-inhibiting pesticides comprising N-methyl carbamate has direct functional and biochemical consequences to the nervous system. The poisonous effects of carbamate pesticides are due to the inhibition of cholinesterase, an enzyme produced in the liver. One form, acetylcholinesterase, can be found in the neurosynaptic junctions while another, butyryl cholinesterase, is primarily located in the plasma and pancreas, although small quantities of it exist in all tissues including blood. Carbamate insecticides inhibit cholinesterase activity in a reversible fashion and normally affect only the plasma fraction.

The cholinergic hypothesis of neurodegenerative diseases such as Alzheimer's disease and Parkinson's disease has spurred the development of structural classes of compounds comprising carbamate moieties aimed at increasing central cholinergic neurotransmission, thus providing a symptomatic treatment for this disease. The most widely used parasympathomimetic, cholinergic agent for the treatment of mild to moderate dementia of the Alzheimer's type and Parkinson's disease is rivastigmine ((S)-N-ethyl-N-methyl-3-[1-(dimethylamino)ethyl]-phenyl carbamate). It has been found that inhibition of acetylecholinesterase (AChE) activity increases the cholinergic transmission and alleviates the dementia symptoms.

Rivastigmine binds to AChE and to ChE via its carbamate moiety, which fits into the enzyme's active site. While the drug is bounded to the enzyme's active site, the carbamate moiety dissociates from the drug molecule, thus leaving the esteratic site of the enzyme carbamylated and producing prolonged inhibition of AChE. The phenolic derivative of rivastigmine is excreted rapidly from the body. Sequestration of AChE in the carbamylated form precludes further enzyme hydrolysis of ACh.

In certain embodiments, the pro-iron chelator function is provided by a quinoline derivative of the formula below, wherein the masking moiety (represented by R'), which may be a moiety that imparts cholinesterase inhibition, is linked to the oxygen at position 8 of the ring. R represents a moiety that imparts a neuroprotection, and/or MAO inhibition, and/or combined antiapoptotic activity and neuroprotection and/or neurorestoration, that may be linked at the 5, 6 and/or 7 positions of the ring. X and Y each independently may be C or N. In certain embodiments, X and Y are both carbon atoms.

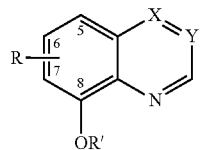

In certain embodiments, the pharmacophore imparting combined iron-chelating and cholinesterase inhibition functions is 8-carbamyloxy-5-quinolinyl, particularly, 8-carbamyloxy-5-quinolinylmethylene.

In certain embodiments, a propargyl amine group is linked to the methylene in position 5 of the 8-carbamyloxy-5-quinolinylmethylene.

In certain additional embodiments, the propargyl amine group is linked to the 5-quinolinylmethylene via piperazine, and R at position 5 is 1-ethylene-4-propargyl piperazine, namely a propargyl group linked to the.

Examples of compounds containing 8-carbamyloxy-5-quinolinylmethylene are the compounds herein designated compound 1, compound 2, compound 5 or compound 11, or the compounds herein designated compound 18, compound 19 or compound 23 in Appendix I.

The pro-chelators 1 to 23, 42 and 43 presented in Appendix I are sometimes referred to herein as "carbamates" since they comprise a carbamate moiety linked to position 8 of a quinoline.

In certain embodiments of the present invention, the iron chelator function is provided by a hydroxamate moiety, a N-hydroxy carbamate [HN(OH)COO—] moiety or a N-alkyl-N-hydroxy carbamate [RN(OH)COO—] moiety.

Hydroxamates are a class of compounds known as iron chelators. For example, desferrioxamine B (Desferal) has been the therapeutic iron chelator of choice for iron-overload treatment, despite numerous problems associated with its use.

In certain embodiments, the hydroxamate group is of the formula HONHC(O)—X, wherein X is an indane or a phenyl group:

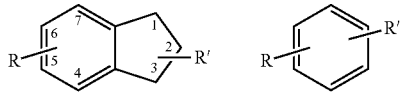

In the iron chelators schematically presented above, R represents one or more iron-chelating groups that may be linked at positions 4, 5, 6 or 7 of the indane, preferably at position 5, or any of the positions 1 to 6 of the phenyl, and R' represents one or more groups which impart neuroprotection, or a combined antiapoptotic and neuroprotective and/or neurorestorative functions, or MAO inhibition, that may be linked to the pentacyclic ring at positions 1, 2 or 3, or at positions 3, 4 or 5 of the phenyl, preferably at the position para to the iron chelating group. The indane and phenyl groups are key structural cores that confer biological activity to the multifunctional compounds. The relative positions of the functional moieties have great impact (either increase or decrease) on the activity of the multifunctional compounds.

In certain embodiments, the multifunctional hydroxamate iron chelators comprise a propargyl amine moiety. In certain embodiments, the hydroxamate is a 2,3-dihydro-N-hydroxy-1H-indene-5-carboxamide and the propargyl amine in linked at the position 3 of the indane.

Examples of compounds containing 2,3-dihydro-N-hydroxy-1H-indene-5-carboxamide and a propargyl amine group are the compounds herein designated compound 24, compound 25 and compound 29 in Appendix I.

In certain embodiments, the hydroxamate is N-hydroxybenzamido and the propargyl amine group is linked at position para on the phenyl.

Examples of multifunctional compounds containing N-hydroxybenzamido and a propargyl amine group are the compounds herein designated compound 32 and compound 34 in Appendix I.

In certain further embodiments, the iron chelating group is N-hydroxy carbamate of the formula HONHC(O)—O—X, wherein X is an indane or a phenyl group. In certain embodiments, the N-hydroxy carbamate is a 2,3-dihydro-N-hydroxy-1H-inden-5-yl carbamate and the propargyl amine moiety is linked at the position 3 of the indane.

Examples of compounds containing 2,3-dihydro-N-hydroxy-1H-inden-5-yl carbamate and a propargyl amine are the compounds herein designated compound 26, compound 27 and compound 30 in Appendix I.

In certain additional embodiments, the N-hydroxy carbamate is N-hydroxyphenyl carbamate and the propargyl amine group is linked at position para to it on the phenyl ring.

Examples of multifunctional compounds containing N-hydroxyphenyl carbamate and a propargyl amine group are the compounds herein designated compound 33 and compound 35 in Appendix I.

Overactivation of N-methyl-D-aspartic acid receptors (NMDARs) by high concentrations of neurotransmitters such as glutamate and NMDA, causes a pathological process by which nerve cells are damaged and killed. Adamantane and derivatives thereof are known antagonists of NMDARs, which act by blocking calcium channels of the receptors.

In certain embodiments, the multifunctional compounds of the invention are designed to protect against NMDA or glutamate toxicity by blocking NMDARs. According to these embodiments, the NMDA antagonist function is provided by an adamantyl moiety.

One group of multifunctional compounds of the invention comprise an NMDA antagonist function, a moiety that imparts combined antiapoptotic and neuroprotective and/or neurorestorative functions and a moiety that imparts brain MAO inhibition. Particularly, these multifunctional compounds comprise mono- or di-propargyl amine groups linked to an adamantane ring. Examples of such compounds are the compounds herein designated compound 36, compound 40 and compound 41 in Appendix I.

In certain embodiments of the invention, the moiety imparting a neuroprotective function to the compound of the invention is selected from the group consisting of a neuroprotective peptide, a neuroprotective peptide fragment and a neuroprotective peptide analog thereof, in which one amino acid residue is replaced by a L- or D-cysteine residue.

The neuroprotective peptide that can be used in the compounds of the invention may be, without being limited to, vasoactive intestinal peptide (VIP), gonadotropin-releasing hormone (GnRH), Substance P and enkephalin.

In certain embodiments, the neuroprotective function is provided by a residue of an analog of VIP, GnRH, Substance P or enkephalin or a fragment thereof, to which the iron-chelating moiety is linked via the —S— atom of the L- or D-Cys moiety.

Examples of neuroprotective peptides, which may be used in the multifunctional compounds of the present invention are the peptides disclosed in WO 2004/041151 herewith incorporated by reference as if fully disclosed herein.

In certain embodiments of the invention, the moiety imparting a neuroprotective function to the compound is a L- or D-cysteine or alanine moiety. In these embodiments, the iron chelator function is attached to the S atom of the Cys moiety.

Drugs with the brain as the site of action should, in general, be able to cross the blood brain barrier (BBB) in order to attain maximal in vivo biological activity. When the intention is to bring drugs to the brain, one of the possible solutions is to design compounds with specific groups, responsible for amphiphilic behavior. Such amphiphilic groups possess lipophilic and hydrophilic centers. The size and structure of both centers control the overall lipophilicity of the whole molecule, and hence its transport properties.

The multifunctional compounds of the present invention are designed to provide the desired blood brain barrier (BBB) transport properties in lipophilic media and are all bioavailable.

Thus, in certain embodiments, the invention relates to compounds comprising the above-mentioned functional moieties and a hydrocarbyl moiety having 1 to 30 carbon atoms, preferably an aliphatic chain. When the pro-iron chelating moiety is a 5-quinolinylmethyl group, the aliphatic chain may be linked directly to the quinoline core itself, or it may be linked via a linker such as ethylenediamine moiety or a piperazine or 1,3,5-perhydrotriazine ring, preferably piperazine, to the 5-quinolinylmethyl group. According to these embodiments, the aliphatic chain of different lengths serves to adjust the size and lipophilicity of the whole molecule, thus controlling the transport properties through the BBB.

When the cholinesterase inhibition function of the compound is attributed to a carbamate moiety, one or two aliphatic chains may be linked to the nitrogen atom, and when the multifunctional compound contains an indane ring, the aliphatic chain may be linked directly or via a linker to the ring. The aliphatic chain may also contain a heteroatom selected from O, S and N.

The present invention encompasses compounds of the formulas I to VI:

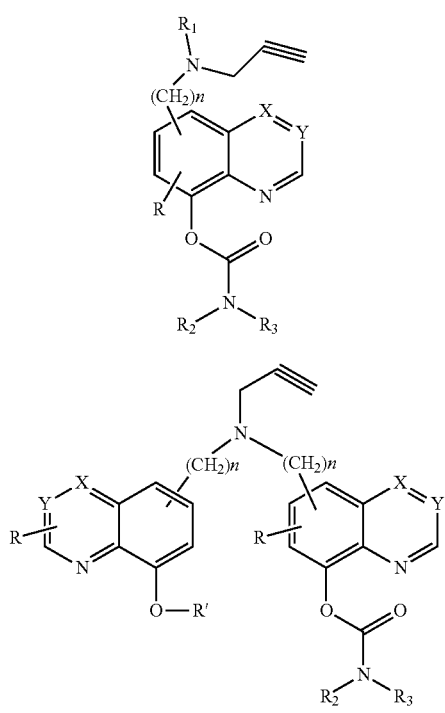

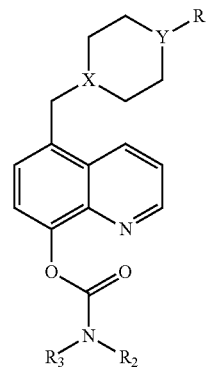

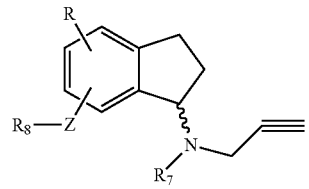

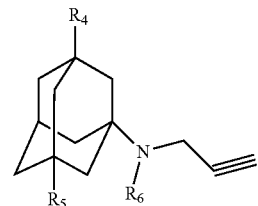

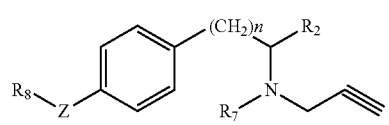

wherein
X and Y each independently is CH or N;
$R_1$ is H or $C_1$-$C_6$ alkyl;
R' is H or $-CONR_2R_3$
R, $R_2$, $R_3$, $R_4$, $R_5$, $R_6$ and $R_7$ each independently is H or a $C_1$-$C_{30}$) hydrocarbyl; or $R_2$ and $R_3$ together with the nitrogen atom to which they are attached form a 5-7 saturated ring optionally containing a further heteroatom selected from O, N or S, and optionally further substituted by an aralkyl group;
$R_8$ is CON(R)OH;
Z is $(CH_2)_m-$ or O;
n is 1 to 10; and m is 0 to 10;
wherein said $C_1$-$C_{30}$ hydrocarbyl is a radical selected from a straight or branched alkyl, alkenyl, or alkynyl, aryl, aralkyl or cycloalkyl having 1 to 30 carbon atoms;
and a stereoisomer or a pharmaceutically acceptable salt thereof.

The term "alkyl" as used herein refers to a straight or branched alkyl radical having 1-30, preferably 1 to 10, more preferably 1 to 6, carbon atoms and includes, for example, methyl, ethyl, n-propyl, iso-propyl, n-butyl, iso-butyl, tert-butyl, 2,2-dimethylpropyl, n-heptyl, n-hexyl, n-septyl, n-octyl, n-nonyl, $-C_{10}H_{21}$, $-C_{15}H_{31}$, $-C_{16}H_{33}$, $-C_{17}H_{35}$, $-C_{18}H_{37}$, $-C_{20}H_{41}$, and the like.

The term "alkenyl" refers to a straight or branched hydrocarbon radical having 2 to 30, preferably 2 to 10, more preferably 2 to 6, carbon atoms and one or more double bonds, such as a terminal double bond, and includes, for example, vinyl, prop-2-en-1-yl, but-3-en-1-yl, pent-4-en-1-yl, hex-5-en-1-yl, $-C_{16}H_{31}$, $C_{18}H_{35}$ and the like.

As used herein the term "alkynyl" refers to a straight or branched hydrocarbon radical having 2 to 30, preferably 2 to 10, more preferably 2 to 6, carbon atoms and one or more triple bonds, and includes for example ethynyl, propargyl (propynyl), butynyl, octynyl, and the like, more preferably propargyl.

The term "cycloalkyl" refers to a saturated cyclic hydrocarbon radical of 3-30, preferably 3 to 10 carbon atoms such as cyclopropyl, cyclobutyl, cyclohexyl, cycloheptyl, adamantyl and the like, optionally further substituted by an alkyl group.

The term "aryl" refers to an aromatic carbocyclic radical having, preferably, 6 to 14, carbon atoms consisting of a single ring or multiple condensed aromatic rings such as phenyl, naphthyl, carbazolyl and phenanthryl. The term "aryl" as used herein also includes, the condensed structure ($C_6$-$C_{14}$)aryl($C_3$-$C_6$)cycloalkyl, preferably the radical indane.

The term "aralkyl" as used herein refers, preferably, to a ($C_6$-$C_{14}$)aryl($C_1$-$C_6$)alkyl radical such as benzyl, phenethyl, phenylpropyl, phenylhexyl, naphthylmethyl, naphthylethyl, and the like, most preferably benzyl.

In certain embodiments, the multifunctional compounds of the invention is are compounds of the formula I or of the formula II:

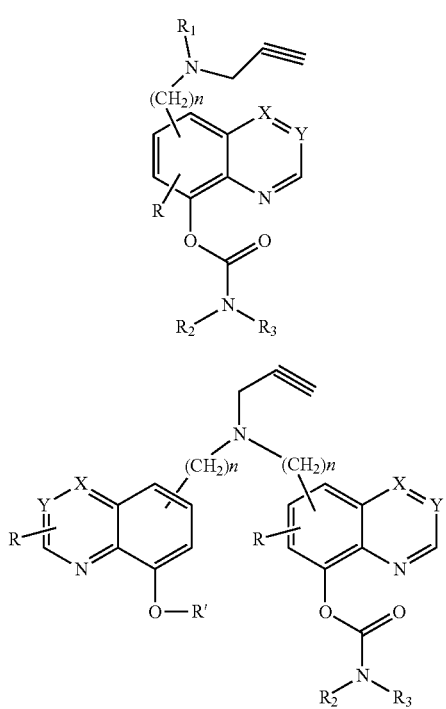

wherein X and Y each independently is CH or N, preferably CH;
R is H or $C_1$-$C_{10}$ hydrocarbyl;
R' is H or —CONR$_2$R$_3$;
$R_1$ is H or $C_1$-$C_3$ alkyl, preferably methyl;
$R_2$ and $R_3$ each independently is selected from:
(i) H;
(ii) $C_1$-$C_{10}$ alkyl, preferably $C_1$-$C_6$ alkyl;
(iii) an optionally substituted $C_3$-$C_{10}$ cycloalkyl, preferably adamantyl optionally substituted by $C_1$-$C_3$ alkyl;
(iv) an optionally substituted ($C_6$-$C_{14}$)aryl, preferably phenyl optionally substituted by a $C_1$-$C_3$ alkyl;
(v) an optionally substituted ($C_6$-$C_{14}$)aryl($C_1$-$C_6$)alkyl, preferably benzyl;
(vi) an optionally substituted ($C_6$-$C_{14}$)aryl($C_3$-$C_6$)cycloalkyl, preferably an indane radical; or
(vii) $R_2$ and $R_3$ together with the nitrogen atom to which they are attached form a 5 or 6 saturated ring optionally containing a further nitrogen atom, and optionally substituted by an aralkyl, preferably benzyl; and n is 1 to 3.

Particular compounds of formula I are selected from the compounds herein designated compounds 1 to 15 (Appendix I).

Particular compounds of formula II are selected from the compounds herein designated compound 42 and compound 43 (Appendix I).

Multifunctional compounds of formula I can be prepared by the method shown in Scheme 1 in Example 1, or by any analogous method. As shown in Scheme 1, compounds of formula I are prepared from the compound M30 disclosed in WO 2004/041151 by reacting M30 with the suitable carbamoyl chloride in a suspension of NaH in THF.

In certain embodiments of the invention, there is provided a multifunctional compound of the formula III:

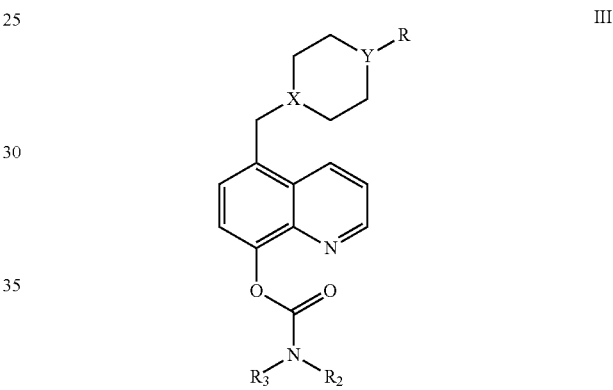

wherein
X, Y each independently is CH or N;
R is a $C_3$-$C_6$ alkynyl, preferably a propargyl group; and
$R_2$ and $R_3$ are as defined above for compound I and II.

Particular multifunctional compound of formula III are selected from the compounds herein designated compounds 16 to 23 (Appendix I).

Multifunctional compounds of formula III can be prepared by the method shown in Scheme 2 in Example 2 or by any analogous method. As shown in Scheme 2, compounds of formula III are prepared from the compound HLA20 disclosed in WO 2004/041151, by reacting HLA20 with the suitable dimethyl carbamoyl chloride in a suspension of NaH in THF.

In certain embodiments, the present invention provides a multifunctional compound of the formula IV:

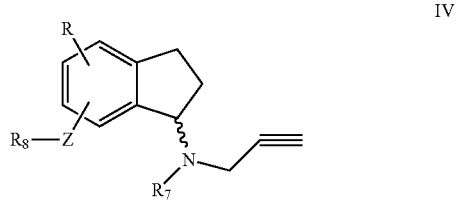

wherein

R and $R_7$ each independently is H or $C_1$-$C_{10}$ hydrocarbyl, preferably $C_1$-$C_3$ alkyl, more preferably methyl;

$R_8$ is —CON(R)OH, preferably —CONHOH;

Z is O or —$(CH_2)_m$—; and m is 0 to 3, preferably 0.

Particular multifunctional compound of formula IV are selected from the compounds herein designated compounds 24 to 31 (Appendix I).

In certain embodiments of the invention, there are provided multifunctional compounds of the formula V:

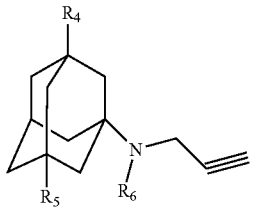

V wherein $R_4$, $R_5$ and $R_6$ each independently is H or $C_1$-$C_{10}$ hydrocarbyl, preferably $R_4$ and $R_5$ is each H or a $C_1$-$C_6$ alkyl and $R_6$ is H, $C_1$-$C_6$ alkyl or $C_2$-$C_6$ alkynyl, preferably propargyl.

Particular multifunctional compounds of formula V are selected from the compounds herein designated compounds 36 to 41 (Appendix I).

In certain additional embodiments, the present invention provides multifunctional compounds of the formula VI:

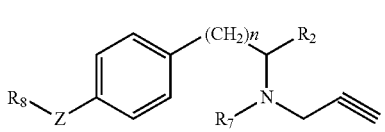

VI wherein $R_2$ and $R_7$ each independently is H or $C_1$-$C_{10}$ hydrocarbyl, preferably H or a $C_1$-$C_6$ alkyl; $R_8$ is —CON(R)OH, preferably —CONHOH; Z is O or —$(CH_2)_m$—; m is 0 to 6, preferably 0; and n is 1 to 6, preferably 1.

Particular multifunctional compound of formula V are selected from the compounds herein designated compounds 32 to 35 (Appendix I).

Also contemplated by the present invention are pharmaceutically acceptable salts of the compounds of formula I to VI, both salts formed by any carboxy groups present in the molecule and a base as well as acid addition and/or base salts.

Pharmaceutically acceptable salts are formed with metals or amines cations, such as cations of alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," (1977) J. of Pharmaceutical Science, 66:1-19).

Pharmaceutically acceptable acid addition salts of basic multifunctional compounds of the invention include salts derived from inorganic acids such as hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc.

Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate or galacturonate (see, for example, Berge S. M., et al., "Pharmaceutical Salts," (1977) J. of Pharmaceutical Science, 66:1-19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The base addition salts of acidic multifunctional compounds of the invention are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

In another aspect, the present invention provides a pharmaceutical composition comprising a multifunctional compound of the invention or an optical isomer thereof or a pharmaceutically acceptable salt thereof, in combination with a pharmaceutically acceptable carrier.

The pharmaceutical composition of the invention is useful for the treatment or prevention of diseases, disorders or conditions that can be prevented and/or treated by iron chelation therapy, and/or neuroprotection and/or neurorestoration, and/or apoptosis inhibition and/or MAO inhibition and/or cholinesterase inhibition and/or NMADR inhibition.

The present invention also provides a cosmetic composition for topical application for prevention and/or treatment of skin ageing and/or skin damage associated with ageing and/or exposure to sunlight and/or UV light. The cosmetic composition may be in the form of a lotion or cream and may be administered with other agents for skin treatment.

For preparing the pharmaceutical and cosmetic compositions of the present invention, methods well known in the art can be used. Inert pharmaceutically and cosmetically acceptable carriers can be used that are either solid of liquid. Solid form pharmaceutical compositions include powders, tablets, dispersible granules, capsules, cachets and suppositories.

A solid carrier can be one or more substances which may also act as diluents, flavoring agents, solubilizers, lubricants, suspending agents, binders, or tablet disintegrating agents; it can also be an encapsulating material.

Liquid pharmaceutical compositions include solutions, suspensions, and emulsions. Examples of liquid formulations include, but are not limited to, water or water-propylene glycol solutions for parenteral injection. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical composition is in unit dosage form. In such form, the preparation is subdivided into unit doses containing appropriate quantities of the active component. The unit dosage form can be a packaged preparation, the package containing discrete quantities of preparation, for example, packeted tablets, capsules, cachets and powders in vial or ampoules.

In a further aspect, the present invention provides the use of a compound of the invention or of an optical isomer thereof or of a pharmaceutically acceptable salt thereof, for preventing and/or treating conditions, disorders or diseases that can be prevented and/or treated by iron chelation therapy, and/or neuroprotection and/or neurorestoration, and/or apoptosis inhibition and/or MAO inhibition and/or cholinesterase inhibition and/or NMADR inhibition.

The multifunctional compounds which comprise an iron chelation function may be used in iron chelation therapy for treatment of diseases, disorders and conditions associated with iron overload and oxidative stress such as iron overload in hemochromatosis and thalassemia, and treatment of anthracycline cardiotoxicity in an individual undergoing treatment with anthracycline neoplastic drugs.

Further diseases, disorders and conditions associated with iron overload and oxidative stress that can be treated or prevented by the multifunctional compounds of the invention include, but are not limited to, neurodegenerative and cerebrovascular diseases and disorders, neoplastic diseases, cardiovascular diseases, diabetes, inflammatory disorders, viral, protozoal and yeast infections, and for retarding ageing, prevention and/or treatment of skin ageing and protecting skin against sunlight and/or UV light.

In certain embodiments, the multifunctional compounds of the invention are useful for iron chelation and neuroprotection in the prevention and/or treatment of neurodegenerative and cerebrovascular diseases, conditions and disorders such as Parkinson's disease, Alzheimer's disease, stroke, amyotrophic lateral sclerosis (ALS), multiple sclerosis, Friedreich's ataxia, Hallervorden-Spatz disease, epilepsy and neurotrauma. Particularly, pharmaceutical compositions comprising said compounds are suitable for treatment of Parkinson's disease, Alzheimer's disease and cerebrovascular disorder, more particularly stroke.

The "prevention" aspect of the use of the multifunctional compounds of the invention in diseases such as Parkinson's disease and Alzheimer's disease involves the prevention of further neurodegeneration and further progress of the disease.

In certain embodiments, the multifunctional compounds of the invention are used for inhibition of cell proliferation in the treatment of neoplastic diseases, wherein all types of cancer being encompassed by the invention. The multifunctional compounds can be used alone or in combination with one or more cytotoxic anticancer drugs.

In certain embodiments, the multifunctional compounds of the invention are used for treatment of depression, mild depression, modest depression, severe depression, and depression associated with another disease or condition such as Parkinson's disease, Alzheimer's disease and vascular dementia.

In certain embodiments, the multifunctional present compounds are used for prevention and/or treatment of cardiovascular diseases, e.g. to prevent the damage associated with free radical generation in reperfusion injury.

In certain embodiments, the present multifunctional compounds are used for prevention and/or treatment of diabetes.

In certain embodiments, the present multifunctional compounds are used for prevention and/or treatment of inflammatory disorders, wherein particular inflammatory disorders treatable according to the invention include, without being limited to, a joint inflammatory disorder, particularly rheumatoid arthritis, inflammatory bowel disease (IBD) and psoriasis.

In certain embodiments, the present multifunctional compounds are used for prevention and/or treatment of viral, protozoal and yeast infections. Particular viral infections treatable according to the invention include, without being limited to, retroviral infections, e.g., HIV-1, wherein the compound used in the treatment of AIDS is optionally used in combination with antiviral agents; protozoal infections preferably malaria caused by *Plasmodium falciparum*; yeast infections, preferably a *Candida albicans* infection.

In certain embodiments, the multifunctional compounds are used for retarding ageing and/or improving the ageing process by prevention of ageing-related diseases, disorders or conditions such as neurodegenerative diseases, disorders or conditions.

In certain embodiments, the multifunctional compounds are used for prevention and/or treatment of skin ageing and/or skin damage associated with ageing and/or exposure to sunlight and/or UV light.

In certain additional embodiments, the multifunctional compounds, particularly those comprising an iron chelating function, are for use ex-vivo for preservation of organs intended for transplantation such as heart, lung or kidney.

In still another aspect, the present invention provides a method for preventing and/or treating conditions, disorders or diseases that can be prevented and/or treated by iron chelation therapy, and/or neuroprotection and neurorestoration, and/or apoptosis inhibition and/or MAO inhibition, and/or cholinesterase inhibition, and/or NMDAR inhibition, said method comprises administering to an individual in need thereof an effective amount of a multifunctional compound of the invention or an optical isomer thereof or a pharmaceutically accepted salt thereof.

In certain embodiments, the present invention provides methods for prevention and/or treatment of neurodegenerative and cerebrovascular diseases, conditions or disorders, comprising administrating to an individual in need thereof an effective amount of a multifunctional compound of the invention. Neurodegenerative diseases treatable according to this method include Parkinson's disease, Alzheimer's disease, stroke, amyotrophic lateral sclerosis (ALS), multiple sclerosis, Friedreich's ataxia, Hallervorden-Spatz disease, epilepsy and neurotrauma. Particular diseases which can be treated by the present methods are Parkinson's disease, Alzheimer's disease and cerebrovascular disorder, more particularly stroke.

In therapeutic use for the treatment of Parkinson's disease, the compounds utilized in the method of the invention may be administered to the patient at dosage levels of from 1 mg/Kg to 20 mg/Kg per day.

In therapeutic use for the treatment of stroke, one or more dosages of from about 100 mg/Kg to about 500 mg/Kg of body weight may be administered to the patient as soon as possible after the event.

In certain embodiments, the methods provided by the invention are for the prevention and/or treatment of cancer. In preferred methods, the compound of the invention is administered before, concurrently or after administration of one or more chemotherapeutic agents.

In certain embodiments, the present methods are for the prevention and/or treatment of iron overload in hemochromatosis or thalassemia patients.

In certain embodiments, the methods provided are for prevention and/or treatment of cardiovascular diseases, or prevention of the damage associated with free radical generation in reperfusion injury.

In certain embodiments, the methods provided by the invention are for prevention and/or treatment of diabetes.

In certain embodiments, the methods provided are for prevention and/or treatment of inflammatory disorders, selected from a joint inflammatory disorder, particularly rheumatoid arthritis, inflammatory bowel disease (IBD), and psoriasis.

In certain additional embodiments, the methods provided are for prevention and/or treatment of anthracycline cardiotoxicity, which comprise administering to an individual undergoing treatment with anthracycline neoplastic drugs an effective amount of a multifunctional compound of the invention or of a pharmaceutically acceptable salt thereof.

In certain embodiments, the methods provided by the invention are for prevention and/or treatment of a viral, protozoal or yeast infection. Viral infection treatable according to said methods are selected from retroviral infections, e,g, HIV-1, and the multifunctional compound used in the treatment of AIDS, is optionally administered in combination with antiviral agents. Protozoal infections treatable according to the invention include malaria caused by *Plasmodium falciparum*, and treatable yeast infections include a *Candida albicans* infection.

In certain embodiments, the method of the invention is for treating depression, mild depression, modest depression, severe depression, and depression associated with another disease or condition such as Parkinson's disease, Alzheimer's disease and vascular dementia.

In certain embodiments, the methods provided are for retarding ageing and/or improving the ageing process by prevention of ageing-related diseases, disorders or conditions. The individual in need may be a healthy individual or an individual suffering from an age-related disease such as a neurodegenerative disease, disorder or condition.

In certain additional embodiments, the methods of the invention are for prevention and/or treatment of skin ageing and/or skin damage associated with ageing and/or exposure to sunlight and/or UV light. The compounds used in said methods are most preferably administered topically in a pharmaceutical or cosmetic formulation.

The dosage, which would be effective in the treatment of any one of the diseases, conditions or disorders mentioned above vary depending upon the requirements of the patient, the severity of the condition being treated, and the compound being employed. Determination of optimum dosages for a particular situation is within the skill of the art.

The following examples illustrate particular methods for the preparation and use of the compounds in accordance with this invention. These examples are intended as an illustration, and not as a limitation, of the scope of the invention.

EXAMPLES

The following examples describe the synthesis of the compounds of the invention (Chemical Section) and their biological activity (Biological Section).

I. Chemical Section

For convenience, the new multifunctional compounds of the invention are designated herein by Arabic numbers 1 to 43. The structural formulas and the chemical names of the compounds 1 to 43 are depicted in Appendix I herein. The multifunctional compounds of the invention include:

1. 5-((methyl(propargyl)amino)methyl)quinolin-8-yl methylcarbamate
2. 5-((methyl(propargyl)amino)methyl)quinolin-8-yl dimethylcarbamate
3. 5-((methyl(propargyl)amino)methyl)quinolin-8-yl ethyl(methyl)carbamate
4. 5-((methyl(propargyl)amino)methyl)quinolin-8-yl hexylcarbamate
5. 5-((methyl(propargyl)amino)methyl)quinolin-8-yl pyrrolidine-1-carboxylate
6. 5-((methyl(propargyl)amino)methyl)quinolin-8-yl piperidine-1-carboxylate
7. 5-((methyl(propargyl)amino)methyl)quinolin-8-yl phenylcarbamate
8. 5-((methyl(propargyl)amino)methyl)quinolin-8-yl o-tolylcarbamate
9. 5-((methyl(propargyl)amino)methyl)quinolin-8-yl 3,5-dimethyladamant-1-ylcarbamate
10. 5-((methyl(propargyl)amino)methyl)quinolin-8-yl adamantylcarbamate
11. (R)-5-((methyl(propargyl)amino)methyl)quinolin-8-yl2,3-dihydro-1H-inden-1-yl carbamate
12. (S)-5-((methyl(propargyl)amino)methyl)quinolin-8-yl 2,3-dihydro-1H-inden-1-yl carbamate
13. 5-((methyl(propargyl)amino)methyl)quinolin-8-yl 4-benzyl piperazine-1-carboxylate
14. 5-((methyl(propargyl)amino)methyl)quinolin-8-yl-4-benzylpiperidine-1-carboxylate
15. 5-((methyl(propargyl)amino)methyl)quinolin-8-yl diethylcarbamate
16. 5-((4-(propargyl)piperazin-1-yl)methyl)quinolin-8-yl methylcarbamate
17. 5-((4-(propargyl)piperazin-1-yl)methyl)quinolin-8-yl dimethylcarbamate
18. 5-((4-(propargyl)piperazin-1-yl)methyl)quinolin-8-yl ethyl(methyl)carbamate
19. 5-((4-(propargyl)piperazin-1-yl)methyl)quinolin-8-yl diethylcarbamate
20. 5-((4-(propargyl)piperazin-1-yl)methyl)quinolin-8-yl pyrrolidine-1-arboxylate
21. 5-((4-(propargyl)piperazin-1-yl)methyl)quinolin-8-yl piperidine-1-carboxylate
22. 5-((4-(propargyl)piperazin-1-yl)methyl)quinolin-8-yl-4-benzylpiperazine-1-carboxylate
23. 5-((4-(propargyl)piperidin-1-yl)methyl)quinolin-8-yl dimethylcarbamate
24. (R)-N-hydroxy-3-(methyl(propargyl)amino)-2,3-dihydro-1H-indene-5-carboxamide
25. (S)-N-hydroxy-3-(methyl(propargyl)amino)-2,3-dihydro-1H-indene-5-carboxamide
26. (R)-3-(methyl(propargyl)amino)-2,3-dihydro-1H-inden-5-yl hydroxycarbamate
27. (S)-3-(methyl(propargyl)amino)-2,3-dihydro-1H-inden-5-yl hydroxycarbamate
28. (R)-N-hydroxy-3-(propargyl)amino)-2,3-dihydro-1H-indene-5-carboxamide
29. (S)-N-hydroxy-3-(propargylamino)-2,3-dihydro-1H-indene-5-carboxamide
30. (R)-3-(propargylamino)-2,3-dihydro-1H-inden-5-yl hydroxycarbamate
31. (S)-3-(propargylamino)-2,3-dihydro-1H-inden-5-yl hydroxycarbamate
32. N-hydroxy-4-((methyl(propargyl)amino)methyl)benzamide
33. 4-((methyl(propargyl)amino)methyl)phenyl hydroxycarbamate
34. N-hydroxy-4-(2-(methyl(propargyl)amino)propyl)benzamide
35. 4-(2-(methyl(propargyl)amino)propyl)phenyl hydroxycarbamate
36. N-(3,5-dimethyl-1-adamantyl)-N-methyl-propargylamine
37. N-adamant-1-yl-N-methylpropargylamine
38. N-(3,5-dimethyl-1-adamantyl)propargylamine
39. N-adamant-1-yl propargylamine
40. N-(3,5-dimethyl-1-adamantyl)-dipropargylamine
41. N-adamant-1-yl dipropargylamine 42. 5-((((8-hydroxyquinolin-5-yl)methyl)(propargyl)amino)methyl)quinolin-8-yl dimethyl carbamate
43. 5,5'-(propargylazanediyl)bis(methylene)bis(quinoline-8,5-diyl)bis(dimethyl carbamate)

(ii) General

Starting materials for chemical synthesis were obtained from the following companies: Aldrich (USA), E. Merck (Germany), Fluka, (Switzerland).

Proton NMR spectra were measured on a Bruker WH-270, a Bruker DPX-250, or a Bruker AMX-400 NMR spectrometer. Flash column chromatography separations were performed on silica gel Merck 60 (230-400 mesh ASTM). UV/VIS spectra were measured on a Hewlett-Packard 8450A diode array spectrophotometer. TLC was performed on E. Merck Kieselgel 60 $F_{254}$ plates. Staining of TLC plates was done by: (i) basic aqueous 1% $KMnO_4$; (ii) 0.3% ninhydrin in $EtOH_{abs}$. Tetrahydrofuran was distilled over $LiAlH_4$ and passed through an $Al_2O_3$ column. Mass spectra (DI, EI-MS) were measured on a VG-platform-II electrospry single quadrupole mass spectrometry (Micro Mass, UK).

Example 1

Synthesis of Compounds of General Formula I (Appendix I)

Scheme 1

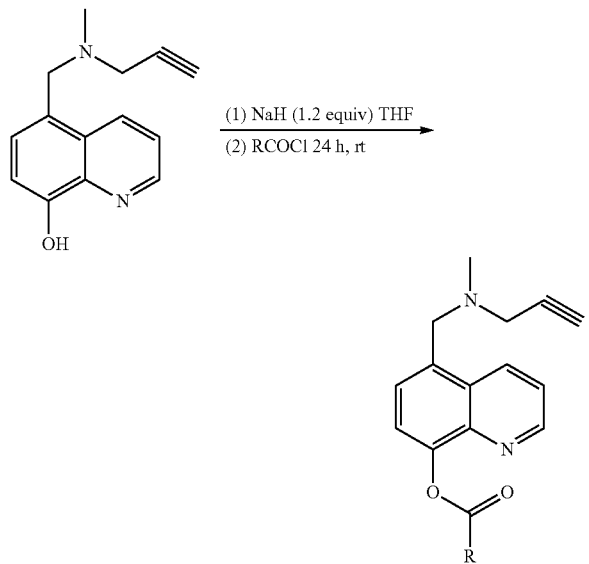

Compounds of formula I were synthesized starting from the compound M30 disclosed in WO 2004/041151, as generally described in Scheme 1, as follows:

To a suspension of NaH (1.2 equiv) in anhydrous THF, M30 (1.0 equiv) was added under Ar at 0° C. The resulting mixture was stirred for 20 min at 0° C. A solution of the corresponding carbamoyl chloride (1.1 equiv) in anhydrous THF was added, and the stirring was continued for 24 h at room temperature. After evaporation of the solvent, water was added and the resulting mixture was extracted with ethyl acetate. The combined organic extracts were washed with brine and dried with $NaSO_4$. Evaporation of the solvent gave a crude product that was purified by flash chromatography or by RP HPLC.

(i) Synthesis of 5-((methyl(propargyl)amino)methyl) quinolin-8-yl piperidine-1-carboxylate (compound 6)

Compound 6 was synthesized by reacting M30 with piperidine-1-carbonyl chloride under the reaction conditions described above. Yield: 76%.
$H^1$ NMR (250 MHz, $D_2O$), 1.09 (m, 6H), 2.50 (dd, J=15.0, 1.50 Hz, 3H), 3.01 (m, 4H), 3.64 (s, 2H), 4.33 (s, 2H), 7.49 (dd, J=8.25, 1.75 Hz, 1H), 7.78 (m, 2H), 8.75 (dd, J=5.50, 1.25 Hz, 1H), 8.99 (dd, J=8.75, 1.25 Hz, 1H). $^{13}C$ NMR (63 MHz, hydrochloric salt in $D_2O$): 26.17, 27.73, 28.05, 42.93, 48.0, 48.52, 48.98, 56.36, 74.15, 84.09, 126.35, 127.21, 129.08, 131.96, 135.08, 138.08, 146.28, 146.42, 148.42, 155.91. Mass spectrometry: calculated for $C_{20}H_{23}N_3O_2$ m/z $[M+Na]^+$=360.42, found $[M+Na]^+$=360.60.

(ii) Synthesis of 5-((methyl(propargyl)amino)methyl)quinolin-8-yl pyrrolidine-1-carboxylate (compound 5)

Compound 5 was synthesized by reacting M30 with pyrrolidine-1-carbonyl chloride under the reaction conditions described above. Yield: 78%.
$H^1$ NMR (250 MHz, $D_2O$), 1.66 (m, 4H), 2.71 (s, 3H), 2.93 (s, 1H), 3.14 (dd, J=5.75, 5.75 Hz, 2H), 3.46 (dd, J=6.0, 6.0 Hz 2H), 3.82 (s, 2H), 4.63 (s, 2H), 7.72 (d J=8.0 Hz, 1H), 7.99 (m, 2H), 8.95 (d, J=5.50, Hz 1H), 9.21 (d, J=8.75 Hz, 1H). $^{13}C$ NMR (63 MHz, hydrochloric salt in $D_2O$) 27.30, 28.00, 42.84, 47.91, 49.81, 56.23, 74.07, 84.04, 126.30, 127.25, 129.32, 131.88, 134.91, 138.09, 145.85, 146.49, 148.32, 155.35.

(iii) Synthesis of 5-((methyl(propargyl)amino)methyl)quinolin-8-yl dimethylcarbamate (compound 2)

Compound 2 was synthesized by reacting M30 with dimethylcarbamic chloride under the reaction conditions described above. Yield: 85%.
$H^1$ NMR (250 MHz, $D_2O$), 2.56 (s, 6H), 2.77 (m, 1H), 2.80 (s, 3H), 3.67 (s, 2H), 4.44 (s, 2H), 7.55 (d, J=8.0 Hz, 1H), 7.80 (m, 2H), 8.79 (d, J=5.50 Hz, 1H), 9.06 (d, J=8.75 Hz, 1H). $^{13}C$ NMR (63 MHz, hydrochloric salt in $D_2O$) 39.46, 39.51, 42.91, 47.98, 56.31, 74.14, 84.09, 126.33, 127.30, 129.33, 131.91, 134.95, 138.10, 146.04, 146.53, 148.35, 157.21. Mass spectrometry: calculated for $C_{20}H_{23}N_3O2$ m/z $[M+H]^+$=298.35, found $[M+H]^+$=298.53.

(iv) Synthesis of 5-((methyl(propargyl)amino)methyl)quinolin-8-yl diethylcarbamate (compound 15)

Compound 15 was synthesized by reacting M30 with diethylcarbamic chloride under the reaction conditions described above. Yield: 80%.
$H^1$ NMR (250 MHz, $D_2O$): 0.762 (dd, J=14.25, 7.25 Hz, 3H), 0.882 (dd, J=14.25, 7.25 Hz, 3H), 2.58 (s, 3H), 2.80 (m, 1H), 2.99 (dd, J=14.25, 7.25 Hz, 2H), 3.24 (dd, J=14.25, 7.25 Hz, 2H), 3.67 (s, 2H), 4.36 (s, 2H), 7.50 (d, J=8.0 Hz, 1H), 7.73 (m, 2H), 8.74 (m, 1H), 8.88 (dd, J=8.75, 1.25 Hz, 1H). $^{13}C$ NMR (63 MHz, hydrochloric salt in $D_2O$) 14.99, 15.95, 42.80, 45.58, 45.67, 47.93, 56.52, 74.13, 83.88, 126.22, 127.24, 128.14, 131.81, 137.34, 143.95, 147.50, 149.70, 157.29. Mass spectrometry: calculated for $C_{19}H_{23}N_3O_2$ m/z $[M+Na]^+$=348.18, found $[M+Na]^+$=348.34.

(v) Synthesis of 5-((methyl(propargyl)amino)methyl) quinolin-8-yl ethyl(methyl) carbamate (compound 3)

Compound 3 was synthesized by reacting M30 with ethyl(methyl)carbamic chloride under the reaction conditions described above. Yield: 82%.

H[1] NMR (250 MHz, D$_2$O), 0.80 (m, 3H), 2.57 (s, 1H), 2.62 (s, 3H), 2.83 (s, 3H), 3.10 (m, 2H), 3.72 (s, 3H), 4.73 (s, 3H), 7.59 (d, J=8.0 Hz, 1H), 7.90 (m, 2H), 8.86 (d, J=5.25 Hz, 1H), 9.13 (d, J=8.75 Hz, 1H). $^{13}$C NMR (63 MHz, hydrochloric salt in D$_2$O) 14.08, 15.05, 36.83, 42.75, 47.40, 47.78, 56.08, 73.94, 84.02, 126.23, 127.03, 129.15, 131.73, 134.71, 137.99, 146.46, 148.21, 156.45. Mass spectrometry: calculated for $C_{18}H_{21}N_3O_2$ m/z [M+Na]$^+$=334.38, found [M+Na]$^+$=334.51.

(vi) Synthesis of 5-((methyl(propargyl)amino)methyl)quinolin-8-yl 4-benzyl piperazine-1-carboxylate (compound 13)

Compound 13 was synthesized by reacting M30 with 4-benzylpiperazine-1-carbonyl chloride under the reaction conditions described above. Yield: 75%.

H[1] NMR (250 MHz, D$_2$O), 2.56 (s, 3H), 2.80 (m, 1H), 2.85-4.26 (m, 8H), 3.98 (s, 2H), 4.37 (s, 4H), 7.04 (s, 5H), 7.60 (d, J=8.0 Hz, 1H), 7.80 (m, 2H), 8.77 (d, J=5.25 Hz, 1H), 9.0 (d, J=8.75 Hz, 1H). $^{13}$C NMR (63 MHz, hydrochloric salt in D$_2$O) 42.87, 43.92, 44.62, 47.97, 53.23, 53.36, 56.30, 63.41, 74.09, 84.03, 126.36, 127.82, 129.36, 130.67, 131.95, 132.14, 133.23, 134.14, 135.26, 137.88, 145.68, 146.03, 148.72, 155.41.

Example 2

Synthesis of 5-((4-(propargyl)piperidin-1-yl)methyl) quinolin-8-yl dimethylcarbamate (compound 23)

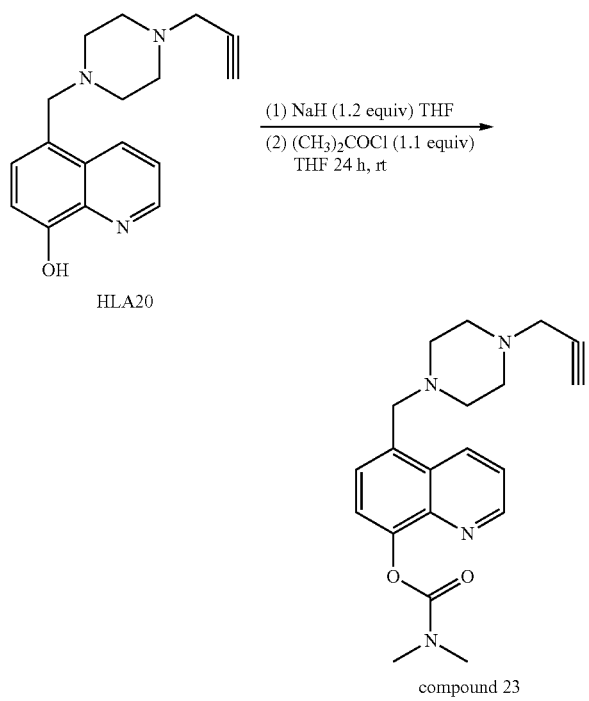

Scheme 2

Compound 23 was synthesized starting from the compound HLA20 disclosed in WO 2004/041151, as described in Scheme 2, as follows:

To a suspension of NaH (24 mg, 0.6 mmol 1.2 equiv) in anhydrous THF, HLA20 (140 mg, 0.5 mmol, 1.0 equiv) was added under Ar at 0° C. The resulting mixture was stirred for 20 min at 0° C. A solution of dimethyl carbamoyl chloride (1.1 equiv) in anhydrous THF was added, and the stirring was continued for 24 h at room temperature. After evaporation of the solvent, water was added and the resulting mixture was extracted with ethyl acetate. The combined organic extracts were washed with brine and dried with NaSO$_4$. Evaporation of the solvent gave a crude product that was purified by RP HPLC.

Yield: 86%.

H[1] NMR (250 MHz, D$_2$O), 2.64 (s, 3H), 2.74 (m, 1H), 3.30 (m, 8H), 3.75 (s, 2H), 4.38 (m, 2H), 7.56 (d, J=8.0 Hz, 1H), 7.83 (m, 2H), 8.80 (m, 1H), 9.10 (d, J=8.75 Hz, 1H). $^{13}$C NMR (63 MHz, hydrochloric salt in D$_2$O): 39.43, 39.50, 48.59, 51.12, 51.80, 58.49, 58.92, 73.49, 83.78, 126.22, 127.40, 129.07, 132.09, 135.56, 137.94, 146.30, 146.40, 148.64, 157.52.

Example 3

Metal Chelation Assay

Metal chelation, particularly iron chelation, is an important precondition for the antioxidative-function of the multi-functional compounds of the invention, because it is the excessive iron stores and iron-mediated generation of free radicals in the brain that are thought to be associated with neurodegenerative diseases. The novel strategy, according to the present invention, for the treatment of neurodegenerative diseases such as Alzheimer's disease is the design of pro-chelators that inhibit AChE with a concomitant release of the active chelators. This novel strategy has advantages over the current chelator strategy since it is capable not only of minimizing the potential toxicity associated with strong chelators such as the 8-hydroxyquinoline derivatives disclosed in WO 2004/041151, which might interfere with healthy metal metabolism in the brain, but it also offers multiple activities against AChE, Aβ aggregation, oxidative stress, and metal (Fe, Cu, Zn) dyshomeostasis in the brain. Therefore, a metal chelation assay was used to confirm that the new multifunctional pro-chelators that comprise an N,N-dialkylcarbamoyl moiety [N(RR')CO—] linked to the oxygen at position 8 of quinoline would have little to no affinity for metal ions in their pro-drug form. When these pro-chelators bind to cholinesterase or AChE in the brain, the N,N-dialkylcarbamoyl moiety is dissociated, thus unmasking a free hydroxyl group at said position 8 of quinoline, turning the pro-chelators into active chelators, which passivate excess cerebral metal ions and protect neuronal cells against reactive oxygen species (ROS).

A spectrophotometric method was used for measurement of metal complexes of the multifunctional pro-chelators of the invention with metal ions selected from $Zn^{2+}$, $Cu^{2+}$, $Fe^{3+}$ and $Fe^{2+}$, and compared to the respective metal complexes of some known iron chelators disclosed in WO 2004/041151.

Thus, the metal chelating function of compound 13 and compound 23 as compared to M30 and HLA20, respectively, was measured by dissolving 0.1 mM or 0.2 mM of the test compounds in 5% NH$_4$Ac, pH=7, in the presence and absence of 0.1 mM or 0.2 mM of the metal salts $ZnCl_3$, $CuSO_4$, $FeCl_3$ and $FeSO_4$, and measuring the UV-vis spectra (Hewlett-Packard 8450A diode array spectrophotometer) of the various metal complexes formed. The results for M30 and compound 13 are shown in FIGS. 1A and 1B, respectively.

Figure 1A:
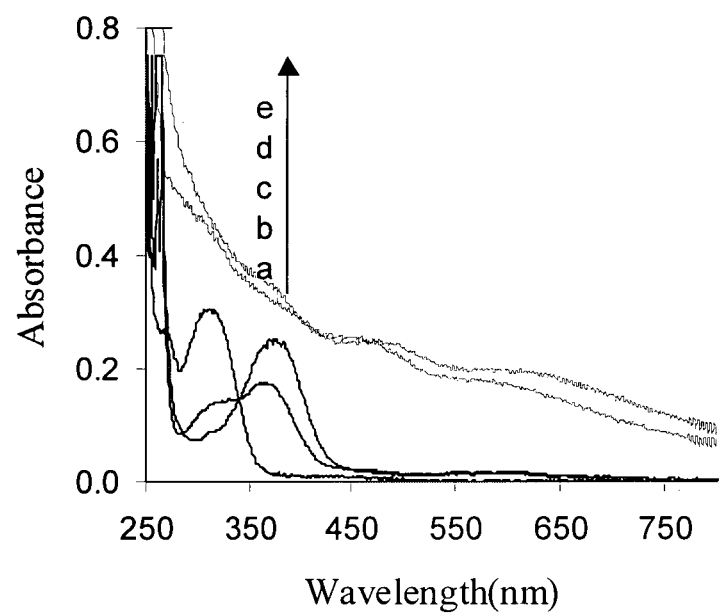
Figure 1B:
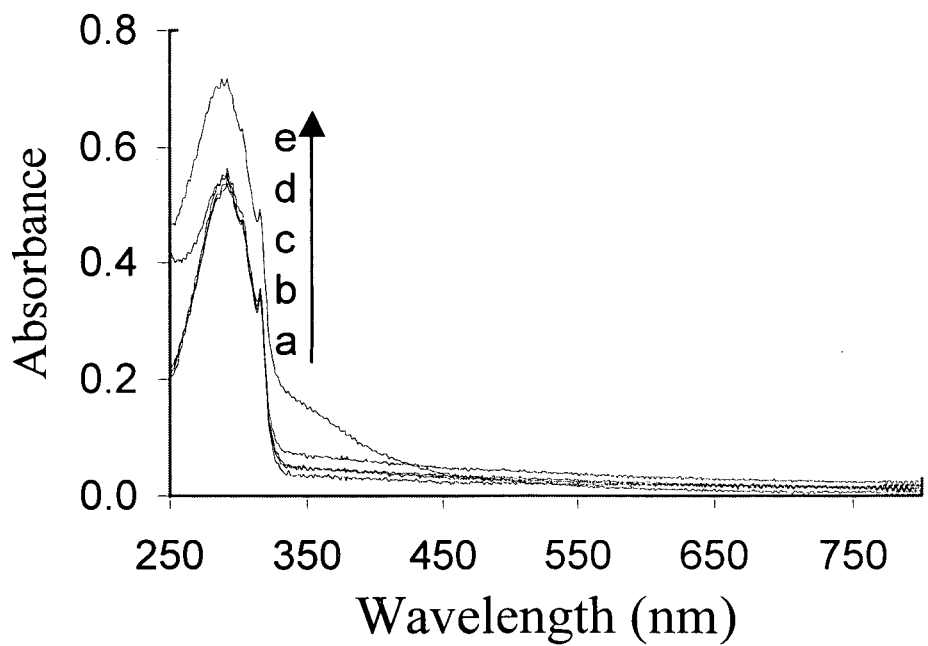

As seen in FIG. 1A, addition of each of one of the metal salts $ZnCl_2$, $CuSO_4$, $FeCl_3$ and $FeSO_4$ to M30, resulted in shifting of the absorbance peak for M30 to higher wavelengths, indicating that the metal chelator binds the respective metal ions. On the other hand, as demonstrated in FIG. 1B, new bands in the in the spectrum of 13 in the UV/VIS region appeared upon the addition of $CuSO_4$ or $ZnCl_2$ to a solution of M30P, suggesting there was little or no complexation between compound 13 and $Cu^{2+}$ or $Zn^{2+}$. Addition of $FeCl_3$ or $FeSO_4$ to a solution of 13 resulted in a slight increase in absorbance at 300 nm, which may indicate a weak interaction.

It is known that 8-quinolinol/Fe complex derivatives have two characteristic absorption bands at around 460 nm and 590 nm. The absence of new such characteristic bands in FIG. 1B suggests that tight Fe-compound 13 complexes did not form.

However, addition of $FeCl_3$ or $FeSO_4$ to an extract from a solution of AChE to which compound 13 was added, resulted in two new bands at around 460 nm and 590 nm exactly matching those in FIG. 1A corresponding to M30–Fe complex. When $ZnCl_2$, or $CuSO_4$ were titrated into the extract, two new bands at around 365 nm or 375 nm appeared, corresponding to the formation of compound 13–Zn complex and compound 13–Cu complex, respectively. These results suggest that compound 13 was converted by AChE back into M30, which exhibits metal (Fe, Zn, and Cu) chelating capacities. This finding was reinforced by mass spectrometry analysis of the extract, which gave a value of m/z 227.22, corresponding to m/z of [M30+H]+.

Figure 2A:
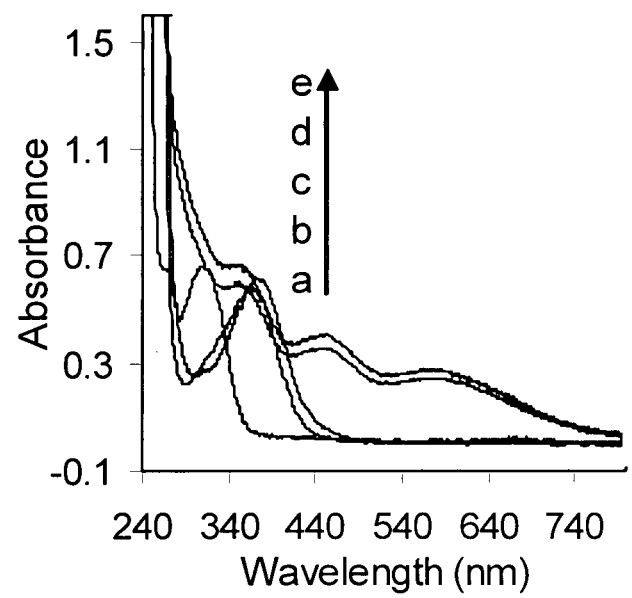
Figure 2B:
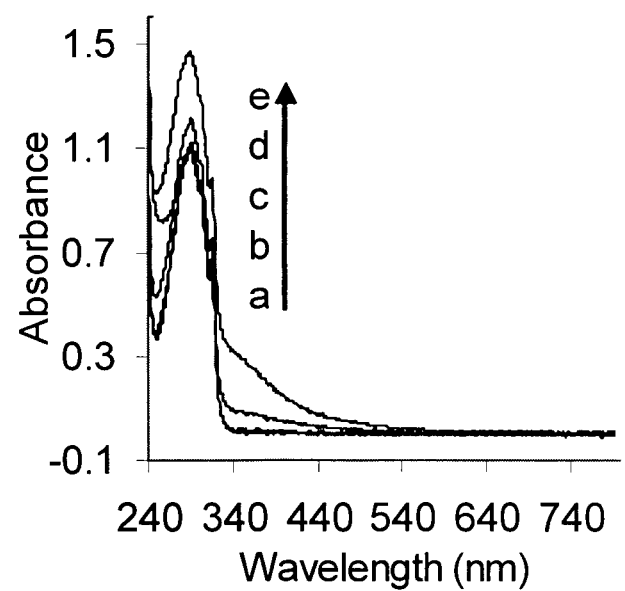

FIGS. 2A and 2B depict the results obtained for HLA20 and compound 23, respectively. As shown in FIG. 2A, addition of each one of the metal salts $ZnCl_2$, $CuSO_4$, $FeCl_3$ and $FeSO_4$ to HLA20 resulted in shifting of the absorbance peak of HLA20 to higher wavelengths, indicating that the metal chelator binds the respective metal ions. FIG. 2B shows that addition of either $CuSO_4$ or $ZnCl_2$ to a solution of 23 did not result in any significant changes in the 200-700 nm absorption spectra, suggesting there was little or no complexation between 23 and $Cu^{2+}$ or $Zn^{2+}$. Addition of $FeCl_3$ or $FeSO_4$ to a solution of compound 23 produced a slight increase in absorbance at 300 nm, which may indicate a weak interaction. The absence of new features suggests that tight Fe-complexes did not form.

When $FeCl_3$ or $FeSO_4$ were titrated to an extract from a solution of AChE into which compound 23 was added, new bands at around 460 nm and 590 nm appeared exactly matching the absorption of HLA20–Fe in FIG. 2A. Titration of $CuSO_4$ or $ZnCl_2$ to the extract introduced new bands at around 370 nm or 360 nm, corresponding to the absorption of the complexes compound 23–Cu and compound 23–Zn, respectively. These results suggest that AChE converted compound 23 back into HLA20 that interacts with metal (Fe, Zn, and Cu) ions and forms metal complexes.

II. Biological Section

Materials and Methods

Cell culture. Human neuroblastoma SH-SY5Y cells were obtained from American Type Culture Collection (Rockville, Md., USA). Cells were routinely cultured in MEM-Eagle/F-12(HAM) (1:1), containing 10% FCS and a mixture of 2% sodium bicarbonate, 1% penicillin/streptomycin/nystatin and 1% sodium pyruvate. Cell cultures were incubated at 37° C. in a humid 5% $CO_2$-95% air environment.

Animals. Male Sprague-Dawley rats (200-250 g) were purchased from Harlan (Rehovot, Israel) and kept in a temperature-controlled room. Animal care was in accordance with the National Institutes of Health Guide for Care and Use of Laboratory Animals and was approved by the Animal Ethics Committee of the Technion, Haifa, Israel.

MTT Tests for Cell Viability.

Twenty-four hours after attachment of the SH-SY5Y cells, the medium was replaced with DMEM containing 0.1% BSA. The test compounds were added to the cells after 1 h of incubation. After 24 h incubation, the cells were subjected to MTT test as previously described (Gassen et al., 1998). The absorption was determined in a Perkin-Elmer Dual Wavelength Eliza-Reader at λ=570/650 nm after automatic subtraction of background readings. The results are expressed as percentage of the untreated control.

Kinetics of Irreversible Cholinesterase Inhibition

To determine kinetic constants of irreversible inhibition, cholinesterase from rat brain homogenates was incubated with the multifunctional compounds of the invention for designed time intervals in phosphate buffer pH 7.4.

The residual cholinesterase activity was immediately measured with the Ellman's colorimetric method after addition of 5,5'-dithiobis(2-nitrobenzoic) acid and 1 mM acetylthiocholine iodide. The inhibition kinetics were assessed according to Kitz-Wilson equation:

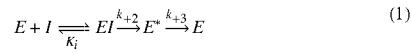

$$E + I \underset{K_i}{\rightleftharpoons} EI \xrightarrow{k_{+2}} E^* \xrightarrow{k_{+3}} E \quad (1)$$

$$\ln \frac{E}{E_0} = -k_{app} t \quad (2)$$

$$\frac{1}{k_{app}} = \frac{1}{k_{+2}} + \frac{K_i}{k_{+2}[I]} \quad (3)$$

wherein: E represents the enzyme; I represents the intact carbamate (inhibitor); EI is the initial reversible enzyme complex; E* is the carbamylated enzyme; Ki represents the dissociation constant for EI; $k_{+2}$ is the carbamylation rate constant and $k_{+3}$ is the decarbamylation rate constant; $k_{app}$ is the pseudo-first-order inhibition rate constant; $k_i$, the second-order rate inhibition constant, is approximated by $k_{+2}/K_i$. Under experimental condition $[I] \gg [E_0]$.

According to equation (2), the logarithm of the ratio of the residual cholinesterase activity (E) and the initial cholinesterase activity ($E_0$) is plotted against the time of incubation. The slopes of the lines representing $k_{app}$ were determined by linear regression. By using the double reciprocal plot of $1/k_{app}$ versus $1/[I]$, $k_{+2}$ and $K_i$ were obtained in accordance with equation (3).

Example 4

Cell Viability Assay

The effect of the iron chelators M30 and HLA20 versus that of the pro-chelators 13 and 23, on viability of human SH-SY5Y cells was tested. Human SH-SY5Y neuroblastoma cells were plated in 100-mm culture dishes and cultured in DMEM (4,500 mg/l glucose), containing 10% FCS (fetal calf serum, Bet Haemek, Israel), and 1% of a mixture of penicillin/streptomycin/nystatin. When cells reached the required confluence, they were detached and re-cultured in microtiter plates (96 wells) pre-coated with collagen (10 mg/cm²), in DMEM with 10% of fetal calf serum ($0.5 \times 10^4$ cells/well). Cell viability was tested by the 3-(4,5-dimethylthiazol-2-yl)-2,5-diphenyltetrazolium (MTT) assays after 48 h incubation.

Figure 3:
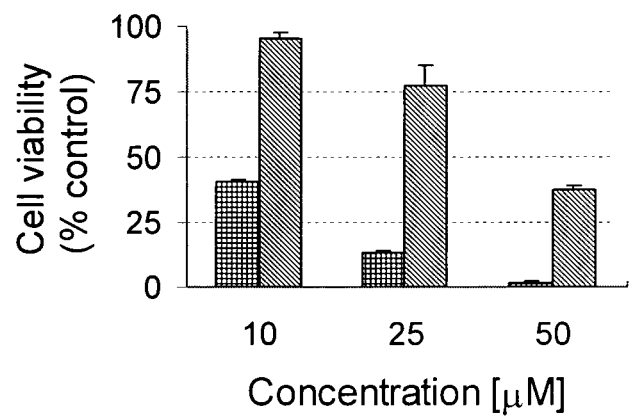
FIG. 3 is a graph showing the effects of HLA20 (■) and compound 23 (☒) on viability of human SH-SY5Y cells. Data are means±SEM of three independent experiments.

Cell viability in the presence of 10, 25 and 50 µM of HLA20 or 23 is depicted in FIG. 3. As shown, cell viability was kept over 75% when cells were treated with 10 µM and 25 µM compound 23, but not with HLA20. At 50 µM 23, cell viability was 40% whereas almost all the cells died in the presence of a similar concentration of HLA20.

Figure 4:
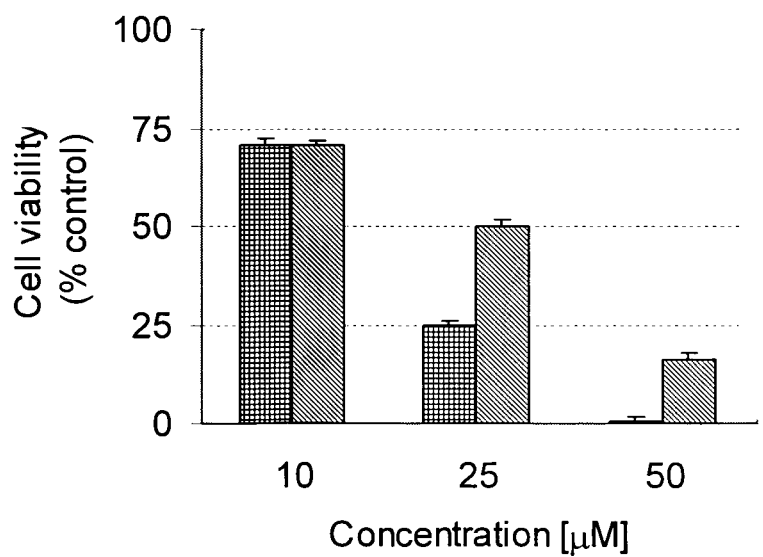
FIG. 4 is a graph showing the effects of M30 (■) and compound 13 (☒) on viability of human SH-SY5Y cells. Data are means±SEM of three independent experiments.

FIG. 4 shows cell viability results for human SH-SY5Y cells treated with 10, 25 and 50 µM of M30 or compound 13. The amount of viable cells was similar in the presence of 10 µM M30 or 13, however, at 25 µM the percentage of viable cells was significantly higher in the presence of 13 as compared to M30.

Example 5

Inhibitory Effects on MAO Activity in Rat Brain

Monoamine oxidase (MAO) exists in two functional forms (isoenzymes): MAO-A and MAO-B, having different substrate and inhibitor specificities.

i. Preparation of Brain MAO

Rats were decapitated and the brains were quickly taken into a pre-weighted ice-cold sucrose buffer (10 mM Tris-HCl buffer, pH 7.4, containing 0.32 M sucrose), and their weights were measured. The brains were homogenized at 0-4° C. in 0.32 M sucrose (one part tissue to 20 parts sucrose) in a Teflon glass homogenizer. The resultant homogenates were used to determine MAO activity. Protein concentration was determined with Bradford reagent at 595 nm, using bovine serum albumin as a standard.

ii. Determination of MAO Activity

The activity of MAO-A and MAO-B were determined by the adapted method of Tipton & Youdim (Tipton et al. 1983). Briefly, the multifunctional compound tested was added to a suitable dilution of the enzyme preparation (70 μg MAO-B and 150 μg MAO-A) in 0.05 M phosphate buffer (pH 7.4). The mixture was incubated together with 0.05 μM 1-deprenyl, a specific inhibitor of MAO-B (for determination of MAO-A activity in the presence of the test compound) or 0.05 μM clorgyline a specific inhibitor of MAO-A (for determination of MAO-B activity). The solutions were incubated 1 hour at 37° C. before addition of $^{14}C$-5-hydroxytryptamine binoxalate (100 μM) for determination of MAO-A, or $^{14}C$-phenylethylamine 100 μM for determination of MAO-B activity, and incubation continued for 30 min or 20 min, respectively. The reaction was stopped with 2M ice-cold citric acid, and the radioactive metabolites (5-hydroxytryptaldehyde and phenylacetaldehyde) were extracted by addition of 2 ml of ethylacetate/toluene (1:1 vol/vol). The radioactivity contained in the organic phase was determined by liquid-scintillation counting in cpm units.

iii. Determination Of Mao Activity in Rat Brain

MAO-A and MAO-B activities were determined in rat brain homogenate in vitro following incubation with varying concentrations of the test compounds. The inhibitory activities of the tested compounds are depicted in Table 1 and shown in FIGS. 5A-5C.

Rat brain cortical homogenates were incubated with the multifunctional chelators of the invention 1 hour after incubating the MAO-A homogenate assay with $10^{-7}$ deprenyl for inhibition of MAO-B, and incubating the MAO-B homogenate assay with $10^{-7}$ clorgyline for inhibition of MAO-A. Then, the homogenates were incubated for 30 min with $^{14}C$-5-hydroxytryptamine or for 20 min with $^{14}C$-β-phenylethylamine, respectively.

The experimental results obtained for compounds 13, 5 and 6 are presented in FIGS. 5A-5C. As shown, all three pro-chelators inhibited both MAO-A and MAO-B, although there were distinct differences in the inhibitory activities of these test compounds. MAO-A was inhibited by compounds 13, 5 and 6 with $IC_{50}$ values in the range of 0.0047-0.020 μM, while 5 and 6 were less effective in inhibiting MAO-B than 13 ($IC_{50}$ values of 5.06 μM and 1.86 μM for 5 and 6, respectively, versus 0.084 μM for 13). HLA20 and compound 23, which were tested as well, showed minor to none inhibitory effects on MAO-A and MAO-B (Table 1).

TABLE 1

| $IC_{50}$ (μM) values or percent inhibition for 10 μM test compound in in vitro inhibition assay of MAO-A and MAO-B | | |
|---|---|---|
| Compound | MAO-A | MAO-B |
| M30 | 0.037 ± 0.02 | 0.057 ± 0.01 |
| 3 | <0.1 | 9% inhibtion (10 μM) |
| 6 | 0.0047 ± 0.0004 | 1.86 ± 0.12 |
| 2 | <0.1 | 67% inhibtion (10 μM) |
| 5 | 0.0049 ± 0.0007 | 5.60 ± 0.34 |
| 13 | 0.020 ± 0.004 | 0.084 ± 0.018 |
| 4 | <0.1 | 25% inhibtion (10 μmM) |

TABLE 1-continued

| $IC_{50}$ (μM) values or percent inhibition for 10 μM test compound in in vitro inhibition assay of MAO-A and MAO-B | | |
|---|---|---|
| Compound | MAO-A | MAO-B |
| 23 | 13% inhibtion (10 μM) | 3% inhibtion (10 μM) |
| HLA20 | 299.8 | 64.2 |

The $IC_{50}$ value is defined as the concentration of compound causing 50% inhibition of MAO activity as determined from concentration response curves by computer assisted linear regression analysis of 8 concentrations. The results are the mean SEM, n=3 in triplicates.

Example 6

Cholinesterase Inhibition Assays

Cholinesterase activity was determined in rat brain homogenate following incubation with varying concentrations of the multifunctional pro-chelators of the invention (also referred to herein as "carbamates"). The inhibitory activities of the tested compounds are depicted in Table 2 and Table 3, and shown in FIGS. 6-8.

Ellman's colorimetric method was adapted for determination of total cholinesterase (ChE) and butyrylcholinesterase (BuChE) activities in rat brain homogenates. Brain tissue from adult Wistar rats was homogenized at 2% w/v (or 10% w/v, for BuChE) in 0.1 M sodium phosphate buffer, pH 7.4, with added NaCl 58.5 g/l and Triton X-100 0.05% v/v. Aliquots of homogenate (20 μl) were incubated with the test compounds for designed time intervals in phosphate buffer pH 7.4, before addition of 5,5'-dithiobis(2-nitrobenzoic) acid and either 1 mM acetylthiocholine iodide or 10 mM butyrylthiocholine iodide (Sigma, St. Louis, Mo.). The reaction was run at 37° C. in a final volume of 200 d in 96-well microplates and was followed at 412 nm for 5 min with a plate reader. In every experiment, cholinesterase-independent (nonspecific) substrate hydrolysis was determined by including one experimental group treated with tacrine 30 μM. Appropriate tissue and reagent blanks were also included. Reaction velocities were determined in three or four replicates per condition; these were averaged and expressed as percent activity relative to control (solvent), after subtracting the rate of nonspecific hydrolysis. All compounds were tested in at least five concentrations that covered the range producing less than 20% and greater than 80% inhibition, but limited to 100 μM.

Results of the concentration-dependent inhibition of total ChE in rat brain homogenates by compounds 6, 3, 2, 5, 13 and 23 are presented in FIGS. 6A-6F, respectively, as obtained independently from three to four experiments. Since the maximum rate of butyrylthiocholine hydrolysis in the absence of inhibitors was about 10% of that of acetylthiocholine hydrolysis when assayed in the same rat brain homogenates, total ChE inhibition largely reflects AChE inhibition. $IC_{50}$ values for all tested compounds or percent inhibition for 1 or 50 μM test compound are summarized in Table 2. The order of inhibitory potency under the present experimental conditions was: 23 (0.50 μM)≥2 (0.52 μM)=13 (0.52 μM)>6 (0.92 μM)>5 (6.4 μM)>3 (9.8 μM)>4 (43% inhibition at 50 μM)>M30 (114 μM). All the tested compounds conferred weak inhibition on BuChE with $IC_{50}$ values in the range of 31-61 μM. With the exception of compound 4, the new carbamates were good AChE inhibitors with high selectivity for AChE over BuChE.

The total ChE inhibition activity of the multifunctional pro-chelators above was determined relative to that of the known inhibitors such as rivastigmine and the results are depicted in Table 2 and shown in FIGS. 8A-8B.

TABLE 2

IC$_{50}$ (μM) values or percent inhibition for 1 μM or 50 μM test compound in in vitro inhibition of ChE and BuChE

| Compound | Total ChE | BuChE |
|---|---|---|
| M30 | 113.86 ± 14.05 | ND |
| 3 | 9.80 ± 0.55 | 60.73 ± 5.33 |
| 6 | 0.92 ± 0.14 | 45.65 ± 5.94 |
| 2 | 0.52 ± 0.07 | 44.90 ± 6.10 |
| 5 | 6.36 ± 0.17 | 31.24 ± 6.10 |
| 13 | 0.52 ± 0.08 | 45.97 ± 3.50 |
| 4 | 43% inhibition (50 μM) | ND |
| 23 | 0.50 ± 0.06 | 42.58 ± 6.67 |
| HLA20 | 40% inhibition (50 μM) | ND |
| Rivastigmine | 62% inhibition (1 μM) | ND |

The IC$_{50}$ value was defined as the concentration of compound causing 50% inhibition of cholinesterase activity as determined from concentration response curves by computer assisted linear regression analysis of 8 concentrations. The results are the mean SEM, n=3 in triplicates. ND—not determined.

The kinetics of inhibition of rat brain cholinesterase (total ChE) with the test compounds are summarized in Table 3 and shown in FIGS. 7A-7L. FIGS. 7A, 7C, 7E, 7G, 7I and 7K present the time and concentration-dependent inhibition of total ChE by compounds 3, 6, 2, 5, 13 and 23, respectively. The slopes of the lines represent the pseudo-first-order inhibition rate constant (k$_{app}$) determined from linear regression analysis. FIGS. 7B, 7D, 7F, 7H, 7J and 7L present the double reciprocal plots of k$_{app}$ as a function of inhibitor concentration (Kitz-Wilson plots) for compounds 3, 6, 2, 5, 13 and 23, respectively. The carbamylation rate constant (k$_{+2}$) was obtained from the y-intercept, and the dissociation constant (IQ was obtained from the slope of the line multiplied by k$_{+2}$ as described in Materials and Methods.

As shown in FIGS. 7A, 7C, 7E, 7G, 7I and 7K, the time course of inhibition displayed pseudo-first-order kinetics at all concentrations used for all the test compounds. From these lines, the values of k$_{app}$ were calculated based on Equation (2) of the Kitz-Wilson equations (see Material and Methods). Double reciprocal plot of 1/k$_{app}$ versus 1/[I] resulted in reasonably good straight lines for all tested carbamates (FIGS. 7B, 7D, 7F, 7H, 7J and 7L), which were used to calculate the kinetic constants (K$_i$, k$_{+2}$ and k$_i$) by linear regression. In general, the lower the K$_i$ value is, the higher is the affinity to the enzyme, while the higher the value of k$_i$ is, the more potent is the inhibitor. As shown in Table 3, all tested carbamates were found to inhibit total ChE activity. 5 exhibited high affinity to total ChE (K$_i$ 69 μM), comparable to that of rivastigmine (K$_i$ 55 μM). 2, 13, and 23 had the highest affinity to total ChE (K$_i$ 9.60, 9.86, 9.66 μM, respectively), followed by 3 and 6 (K$_i$ 11.5 and 15.1 mM, respectively), presenting higher affinity than that of rivastigmine (K K$_i$ 55 μM). The carbamylation rate constant k$_{+2}$ is a measure of inactivation of ChE. The values of k$_{+2}$ in Table 3 indicate that 3 (k$_{+2}$ 0.27) and 2 (k$_{+2}$ 0.30) possessed the fastest rate of carbamylation among the tested carbamates, comparable to that of rivastigmine (k$_{+2}$ 0.25). They were about as 2-3 fold fast as the 5, 13, and 23 (k$_{+2}$ 0.17, 0.1, and 0.14, respectively). 6 (k$_{+2}$ 0.07) displayed the slowest rate of carbamylation among the tested carbamates with about 35-fold slower rate than that of rivastigmine (k$_{+2}$ 0.25). k$_i$, the second-order rate inhibition constant, can correlate with inhibition potencies. The data in Table 3 suggest that 6 was as potent and 4 (k$_i$ 2.34×10$^3$ M$^{-1}$ min$^{-1}$) and 5 (k$_i$ 2.46×10$^3$ M$^{-1}$ min$^{-1}$) were as half potent as rivastigmine in inhibiting ChE, while 2 (k$_i$ 3.13×10$^4$ M$^{-1}$ min$^{-1}$), 13 (k$_i$ 1.01× 10$^4$ M$^{-1}$ min$^{-1}$), and 23 (k$_i$ 1.45×10$^4$ M$^{-1}$ min$^{-1}$) were 2 to 6-fold more potent than rivastigmine.

TABLE 3

Kinetic Parameters for Inhibition of Rat Brain Cholinesterase

| Compound | K$_i$ (M) | k$_{+2}$ (min$^{-1}$) | k$_i$ (M$^{-1}$ min$^{-1}$)$^a$ |
|---|---|---|---|
| 3 | 1.15 × 10$^{-5}$ | 0.27 | 2.34 × 10$^3$ |
| 6 | 1.51 × 10$^{-5}$ | 0.07 | 4.64 × 10$^3$ |
| 2 | 9.60 × 10$^{-6}$ | 0.3 | 3.13 × 10$^4$ |
| 5 | 6.90 × 10$^{-5}$ | 0.17 | 2.46 × 10$^3$ |
| 13 | 9.86 × 10$^{-6}$ | 0.1 | 1.01 × 10$^4$ |
| 4 | ND | ND | ND |
| 23 | 9.66 × 10$^{-6}$ | 0.14 | 1.45 × 10$^4$ |
| HLA20 | ND | ND | ND |
| Rivastigmine | 5.5 × 10$^{-5b}$ | 0.25$^b$ | 4.54 × 10$^{3b}$ |

Each constant represents the mean of 3-4 independent experiments, and r$^2$ ≥ 0.95 for all primary and secondary plots from which the constants were determined (SEM ≤ 12%).
$^a$k$_i$ is the second-order rate inhibition constant, and it is approximated by k$_{+2}$/K$_i$.
$^b$Data from ref.
ND: not determined.

Known carbamate ChE inhibitors such as physostigmine and rivastigmine inhibit ChE in a time-dependent manner and require preincubation in order to exhibit appropriate anti-ChE activity. The new carbamates of the present invention are expected to act as rivastigmine and inhibit ChE activity. In order to assess the maximum ChE inhibition of these carbamates versus that of rivastigmine, ChE from rat brain homogenates was incubated with the new carbamates at 1 μM for the indicated times. Enzyme activity was determined with Ellman's colorimetric method after addition of substrate, and the results are shown in FIGS. 8A-8B.

As seen in FIG. 8A, compound 23 caused increasingly greater inhibition, compared to rivastigmine, in a time-dependent manner, and attained maximum inhibition on total ChE after 2 h preincubation. FIG. 8B shows time-dependent inhibition of compounds 3, 6, 2, 5 and 13 in comparison with that of rivastigmine. 3 and 5 reached their peak inhibition on total ChE within 1.5 h and 3 h, respectively, and were far less potent than the other carbamates. Of all carbamates tested, 2 and 13 turned out to be very good ChE inhibitors with the former more potent than, and the latter as potent as rivastigmine.

REFERENCES

Andrews F. J., Morris C. J., Kondratowicz G., Blake, D. R., (1987) "Effect of iron chelation on inflammatory joint disease", Ann. Rheum. Dis., 46(4):327-33.

Antonov (1995), "Novel adamantane derivatives act as blockers of open ligand-gated channels and as anticonvulsants", Molecular Pharmacology, 47: 558-567.

Ben-Shachar, D., Eshel, G., Finberg, J. P. and Youdim, M. B., (1991) "The iron chelator desferrioxamine (Desferal) retards 6-hydroxydopamine-induced degeneration of nigrostriatal dopamine neurons.", J. Neurochem., 56:1441-1444.

Bissett, D. L. and McBride, J. F., (1996) "Synergistic topical photoprotection by a combination of the iron chelator 2-furildioxime and sunscreen", J. Am. Acad. Dermatol. 35(4):546-9.

Buss, J. L., Torti, F. M., and Torti, S. V., (2003) "The role of iron chelation in cancer therapy", Curr. Med. Chem., 10(12): 1021-34.

Butterfield, D. A., Howard, B. J., and LaFontaine, M. A., (2001) "Brain oxidative stress in animal models of accelerated aging and the age-related neurodegenerative disorders, Alzheimer's disease and Huntington's disease", Curr. Med. Chem., 8(7):815-28.

Cuajungco, M. P., Faget, K. Y., Huang, X., Tanzi, R. E., and Bush, A. I., (2000) "Metal chelation as a potential therapy for Alzheimer's disease", Ann. N.Y. Acad. Sci., 920:292-304.

Flaherty, J. T. and Zweier, J. L., (1991) "Role of oxygen radicals in myocardial reperfusion injury: experimental and clinical evidence", Klin. Wochenschr., 69(21-23):1061-5.

Gassen, M., Gross, A. and Youdim, M. B., (1998) "Apomorphine enantiomers protect cultured pheochromocytoma (PC12) cells from oxidative stress induced by $H_2O_2$ and 6-hydroxydopamine.", Movement Disorders, 13:242-248.

Gassen, M. and Youdim, M. B., (1999) "Free radical scavengers: chemical concepts and clinical relevance", J. Neural. Transm. Suppl., 56:193-210.

Hahn P, Milam A H, Dunaief J L, (2003). "Maculas affected by age-related macular degeneration contain increased chelatable iron in the retinal pigment epithelium and Bruch's membrane", Arch Ophthalmol., 121(8):1099-105.

Hershko, C., (1994) "Control of disease by selective iron depletion: a novel therapeutic strategy utilizing iron chelators", Eur. J. Biochem., 270(8):1689.

Hershko, C, Pinson, A, and Link, G., (1996) "Prevention of anthracycline cardiotoxicity by iron chelation", Acta Haematol., 95(1):87-92.

Hewitt, S. D., Hider, R. C., Sarpong, P., Morris, C. J., and Blake, D. R., (1989) "Investigation of the anti-inflammatory properties of hydroxypyridinones", Annals of Rheum. Diseases, 48:382-388.

Kitazawa, M. and Iwasaki, K., (1999) "Reduction of ultraviolet light-induced oxidative stress by amino acid-based iron chelators", Biochim. Biophys. Acta., 27; 1473(2-3):400-8.

Ostrakhovitch, E. A. and Afanas'ev, I. B., (2001) "Oxidative stress in rheumatoid arthritis leukocytes: suppression by rutin and other antioxidants and chelators", Biochem. Pharmacol., 62(6):743-6.

Polla, A. S., Polla, L. L., Polla, B. S., (2003) "Iron as the malignant spirit in successful ageing", Ageing Res. Rev., 2(1): 25-37.

Roza, A. M., Slakey, D. P., Pieper, G. M., Van Ye, T. M., Moore-Hilton, G, Komorowski, R. A., Johnson, C. P., Hedlund, B. E., and Adams, M. B., (1994) "Hydroxyethyl starch deferoxamine, a novel iron chelator, delays diabetes in BB rats", J. Lab. Clin. Med., 123(4):556-60.

Sayre, L. M., Perry, G, Atwood, C. S, and Smith, M. A., (2000) "The role of metals in neurodegenerative diseases", Cell. Mol. Biol., 46:731-741.

Sobolevsky and Koshelev (1998), "Two Blocking Sites of Amino-Adamantane Derivatives in Open N-Methyl-D-Aspartate Channels", Biophysical Journal 74: 1305-1319.

Sterling et al. 2002, "Novel Dual Inhibitors of AChE and MAO Derived from Hydroxy Aminoindan and Phenethylamine as Potential Treatment for Alzheimer's Disease" J. Medicinal Chem. 45: 5260-5279.

Tipton K. F., Youdim M. B. H. (1983), "The assay of monoamine oxidase activity Methods in Biogenic Amine Research. Amsterdam: Elsevier; 441-467. Parvez, S, Nagatsu, T., Nagatsu, I. & Parvez, H. (eds). pp.

Yogev-Falach et al. (2006), "A multifunctional, neuroprotective drug, ladostigil (TV3326), regulates holo-APP translation and processing" The FASEB Journal, 20:2177-2179

Youdim et al. (1988), "Increased iron (III) and total iron content in post mortem substantia nigra of parkinsonian brain" Journal of Neural Transmission 74, 199-205.

Appendix I

| Compound's number | Chemical name | Structure |
|---|---|---|
| 1 | 5-((methyl(propargyl)amino)methyl)quinolin-8-yl methylcarbamate | 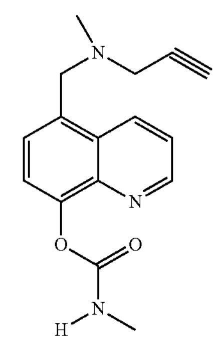 [SMILES: C#CCN(C)Cc1ccc(OC(=O)NC)c2ncccc12] |
| 2 | 5-((methyl(propargyl)amino)methyl)quinolin-8-yl dimethylcarbamate | 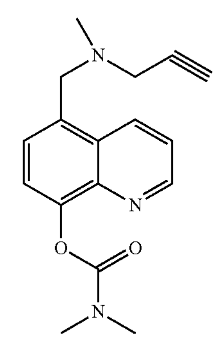 [SMILES: C#CCN(C)Cc1ccc(OC(=O)N(C)C)c2ncccc12] |

Appendix I-continued
| Compound's number | Chemical name | Structure |
|---|---|---|
| 3 | 5-((methyl(propargyl)amino)methyl)quinolin-8-yl ethyl(methyl)carbamate | 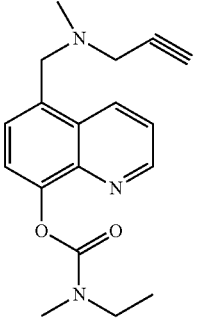 [SMILES: C#CCN(C)Cc1ccc(OC(=O)N(C)CC)c2ncccc12] |
| 4 | 5-((methyl(propargyl)amino)methyl)quinolin-8-yl hexylcarbamate | 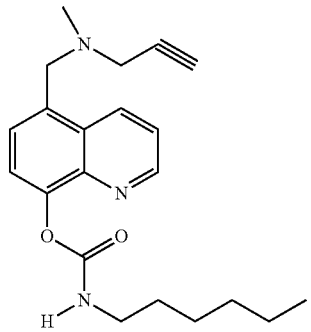 [SMILES: C#CCN(C)Cc1ccc(OC(=O)NCCCCCC)c2ncccc12] |
| 5 | 5-((methyl(propargyl)amino)methyl)quinolin-8-yl pyrrolidine-1-carboxylate | 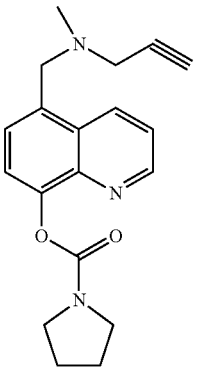 [SMILES: C#CCN(C)Cc1ccc(OC(=O)N2CCCC2)c2ncccc12] |
| 6 | 5-((methyl(propargyl)amino)methyl)quinolin-8-yl piperidine-1-carboxylate | 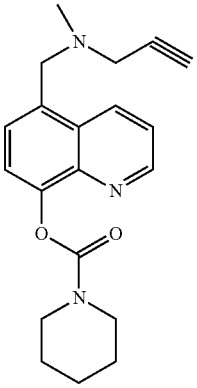 [SMILES: C#CCN(C)Cc1ccc(OC(=O)N2CCCCC2)c2ncccc12] |

Appendix I-continued

| Compound's number | Chemical name | Structure |
|---|---|---|
| 7 | 5-((methyl(propargyl)amino)methyl)quinolin-8-yl phenylcarbamate | 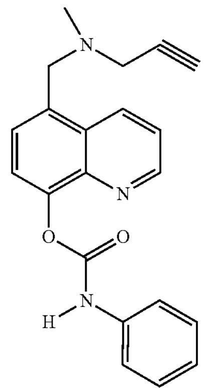 [SMILES: C#CCN(C)Cc1ccc(OC(=O)Nc2ccccc2)c2ncccc12] |
| 8 | 5-((methyl(propargyl)amino)methyl)quinolin-8-yl o-tolyl-carbamate | 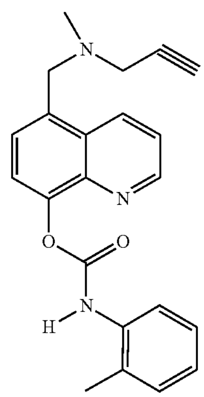 [SMILES: C#CCN(C)Cc1ccc(OC(=O)Nc2ccccc2C)c2ncccc12] |
| 9 | 5-((methyl(propargyl)amino)methyl)quinolin-8-yl 3,5-dimethyladamant-1-ylcarbamate | 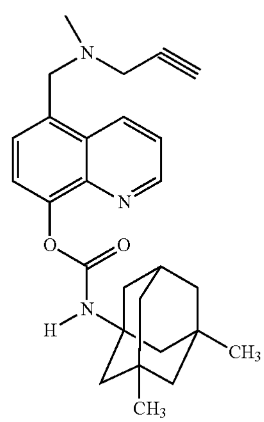 [SMILES: C#CCN(C)Cc1ccc(OC(=O)NC23CC4CC(C)(CC(C)(C4)C2)C3)c2ncccc12] |
| 10 | 5-((methyl(propargyl)amino)methyl)quinolin-8-yl adamantylcarbamate | 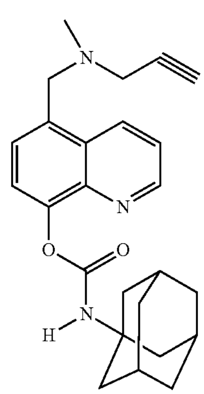 [SMILES: C#CCN(C)Cc1ccc(OC(=O)NC23CC4CC(CC(C4)C2)C3)c2ncccc12] |

Appendix I-continued

| Compound's number | Chemical name | Structure |
|---|---|---|
| 11 | (R)-5-((methyl(propargyl) amino)methyl)quinolin-8-yl 2,3-dihydro-1H-inden-1-yl carbamate | 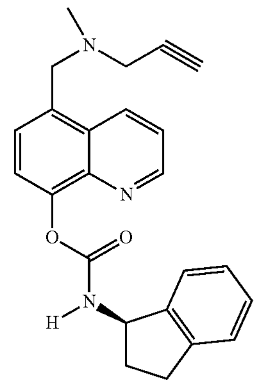 [SMILES: C#CCN(C)Cc1ccc(OC(=O)N[C@@H]2CCc3ccccc32)c2ncccc12] |
| 12 | (S)-5-((methyl(propargyl) amino)methyl)quinolin-8-yl 2,3-dihydro-1H-inden-1-ylcarbamate | 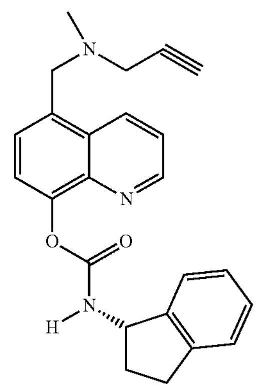 |
| 13 | 5-((methyl(propargyl)amino) methyl)quinolin-8-yl 4-benzyl piperazine-1-carboxylate | 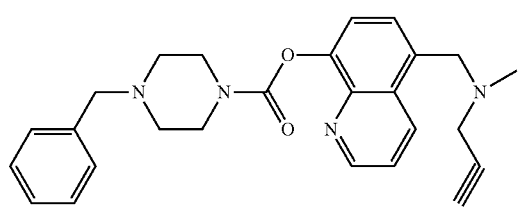 [SMILES: C#CCN(C)Cc1ccc(OC(=O)N2CCN(Cc3ccccc3)CC2)c2ncccc12] |
| 14 | 5-((methyl(propargyl)amino) methyl)quinolin-8-yl-4-benzyl piperidine-1-carboxylate | 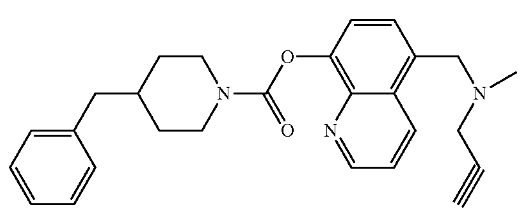 [SMILES: C#CCN(C)Cc1ccc(OC(=O)N2CCC(Cc3ccccc3)CC2)c2ncccc12] |
| 15 | 5-((methyl(propargyl)amino) methyl)quinolin-8-yl diethylcarbamate | 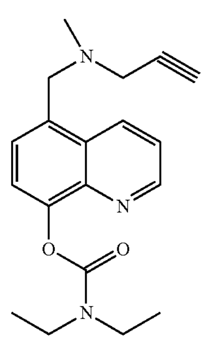 [SMILES: C#CCN(C)Cc1ccc(OC(=O)N(CC)CC)c2ncccc12] |

Appendix I-continued

| Compound's number | Chemical name | Structure |
|---|---|---|
| 16 | 5-((4-(propargyl)piperazin-1-yl)methyl)quinolin-8-yl methylcarbamate | 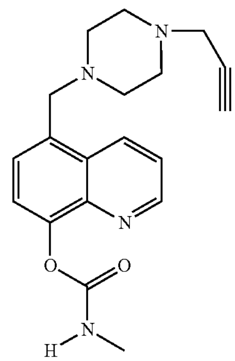 [SMILES: C#CCN1CCN(Cc2ccc(OC(=O)NC)c3ncccc23)CC1] |
| 17 | 5-((4-(propargyl)piperazin-1-yl)methyl)quinolin-8-yl dimethylcarbamate | 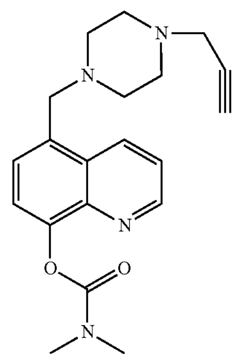 [SMILES: C#CCN1CCN(Cc2ccc(OC(=O)N(C)C)c3ncccc23)CC1] |
| 18 | 5-((4-(propargyl)piperazin-1-yl)methyl)quinolin-8-yl ethyl(methyl)carbamate | 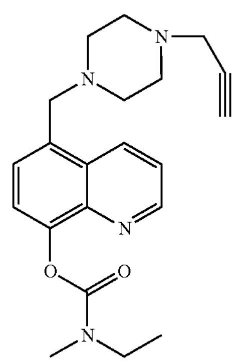 [SMILES: C#CCN1CCN(Cc2ccc(OC(=O)N(C)CC)c3ncccc23)CC1] |
| 19 | 5-((4-(propargyl)piperazin-1-yl)methyl)quinolin-8-yl diethylcarbamate | 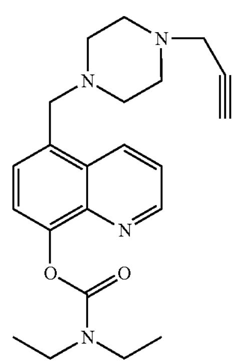 [SMILES: C#CCN1CCN(Cc2ccc(OC(=O)N(CC)CC)c3ncccc23)CC1] |

Appendix I-continued

| Compound's number | Chemical name | Structure |
|---|---|---|
| 20 | 5-((4-(propargyl)piperazin-1-yl)methyl)quinolin-8-yl pyrrolidine-1-carboxylate | 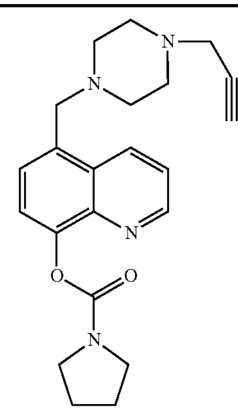 |
| 21 | 5-((4-(propargyl)piperazin-1-yl)methyl)quinolin-8-yl piperidine-1-carboxylate | 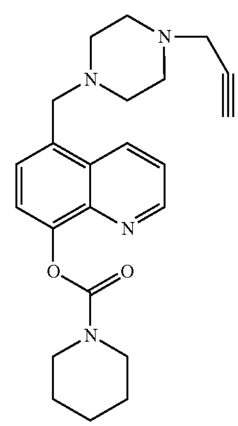 [SMILES: C#CCN1CCN(Cc2ccc(OC(=O)N3CCCCC3)c3ncccc23)CC1] |
| 22 | 5-((4-(propargyl)piperazin-1-yl)methyl)quinolin-8-yl 4-benzylpiperazine-1-carboxylate | 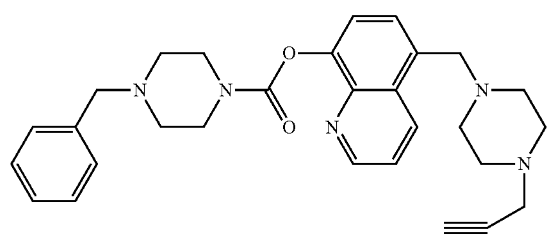 [SMILES: C#CCN1CCN(Cc2ccc(OC(=O)N3CCN(Cc4ccccc4)CC3)c3ncccc23)CC1] |
| 23 | 5-((4-(propargyl)piperidin-1-yl)methyl)quinolin-8-yl dimethylcarbamate | 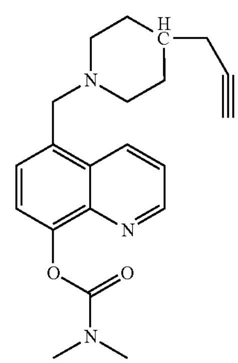 [SMILES: C#CCC1CCN(Cc2ccc(OC(=O)N(C)C)c3ncccc23)CC1] |
| 24 | (R)-N-hydroxy-3-(methyl(propargyl)amino)-2,3-dihydro-1H-indene-5-carboxamide | 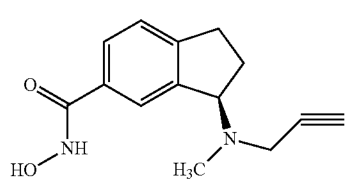 [SMILES: C#CCN(C)[C@@H]1CCc2ccc(C(=O)NO)cc21] |

Appendix I-continued

| Compound's number | Chemical name | Structure |
|---|---|---|
| 25 | (S)-N-hydroxy-3-(methyl(propargyl)amino)-2,3-dihydro-1H-indene-5-carboxamide | 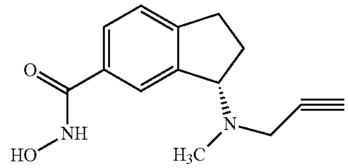 [SMILES: C#CCN(C)[C@H]1CCc2ccc(C(=O)NO)cc21] |
| 26 | (R)-3-(methyl(propargyl)amino)-2,3-dihydro-1H-inden-5-yl hydroxycarbamate | 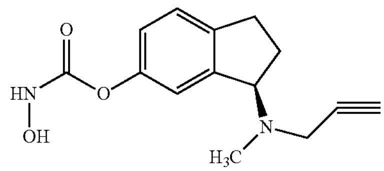 [SMILES: C#CCN(C)[C@@H]1CCc2ccc(OC(=O)NO)cc21] |
| 27 | (S)-3-(methyl(propargyl)amino)-2,3-dihydro-1H-inden-5-yl hydroxycarbamate | 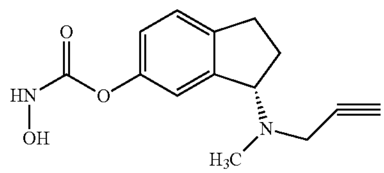 [SMILES: C#CCN(C)[C@H]1CCc2ccc(OC(=O)NO)cc21] |
| 28 | (R)-N-hydroxy-3-(propargyl amino)-2,3-dihydro-1H-indene-5-carboxamide | 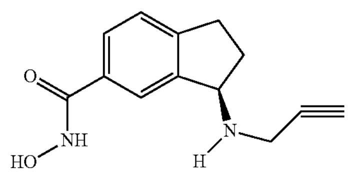 [SMILES: C#CCN[C@@H]1CCc2ccc(C(=O)NO)cc21] |
| 29 | (S)-N-hydroxy-3-(propargylamino)-2,3-dihydro-1H-indene-5-carboxamide | 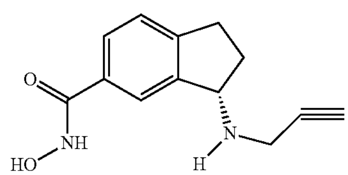 [SMILES: C#CCN[C@H]1CCc2ccc(C(=O)NO)cc21] |
| 30 | (R)-3-(propargylamino)-2,3-dihydro-1H-inden-5-yl hydroxycarbamate | 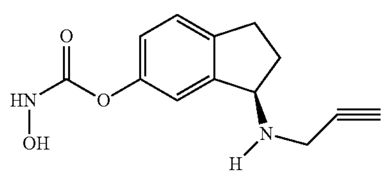 [SMILES: C#CCN[C@@H]1CCc2ccc(OC(=O)NO)cc21] |
| 31 | (S)-3-(propargylamino)-2,3-dihydro-1H-inden-5-yl hydroxycarbamate | 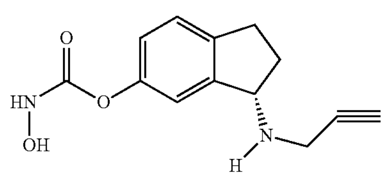 [SMILES: C#CCN[C@H]1CCc2ccc(OC(=O)NO)cc21] |
| 32 | N-hydroxy-4-((methyl(propargyl)amino)methyl)benzamide | 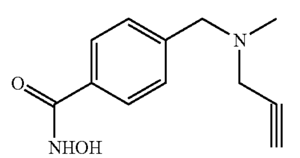 |
| 33 | 4-((methyl(propargyl)amino)methyl)phenyl hydroxycarbamate | 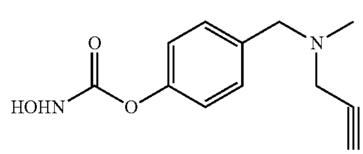 |

Appendix I-continued

| Compound's number | Chemical name | Structure |
|---|---|---|
| 34 | N-hydroxy-4-(2-(methyl(propargyl)amino)propyl)benzamide | 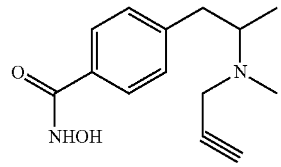 |
| 35 | 4-(2-(methyl(propargyl)amino)propyl)phenyl hydroxycarbamate | 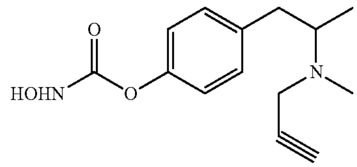 |
| 36 | N-(3,5-dimethyl-1-adamantyl)-N-methyl-propargylamine | 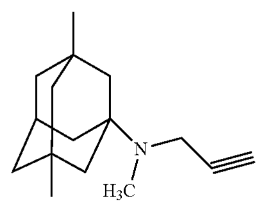 [SMILES: C#CCN(C)C12CC3CC(C)(CC(C)(C3)C1)C2] |
| 37 | N-adamant-1-yl-N-methylpropargylamine | 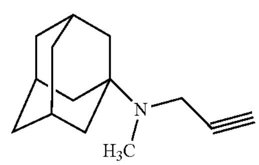 |
| 38 | N-(3,5-dimethyl-1-adamantyl) propargylamine | 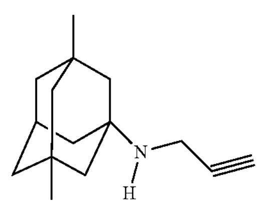 [SMILES: C#CCNC12CC3CC(C)(CC(C)(C3)C1)C2] |
| 39 | N-adamantan-1-yl propargylamine | 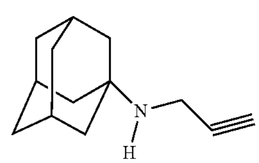 |
| 40 | N-(3,5-dimethyl-1-adamantyl)-dipropargylamine | 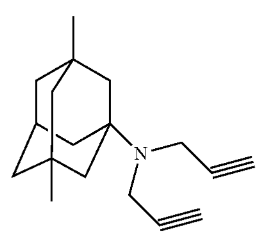 [SMILES: C#CCN(CC#C)C12CC3CC(C)(CC(C)(C3)C1)C2] |

Appendix I-continued
| Compound's number | Chemical name | Structure |
|---|---|---|
| 41 | N-adamant-1-yl dipropargylamine | 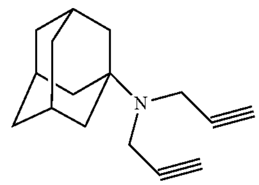 [SMILES: C#CCN(CC#C)C12CC3CC(CC(C3)C1)C2] |
| 42 | 5-((((8-hydroxyquinolin-5-yl)methyl)(propargyl)amino)methyl) quinolin-8-yl dimethylcarbamate | 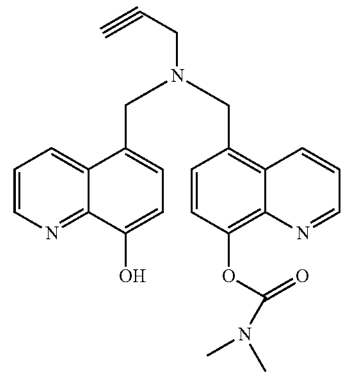 [SMILES: C#CCN(Cc1ccc(O)c2ncccc12)Cc1ccc(OC(=O)N(C)C)c2ncccc12] |
| 43 | 5,5'-(propargylazanediyl)bis (methylene)bis(quinoline-8,5-diyl) bis(dimethylcarbamate) | 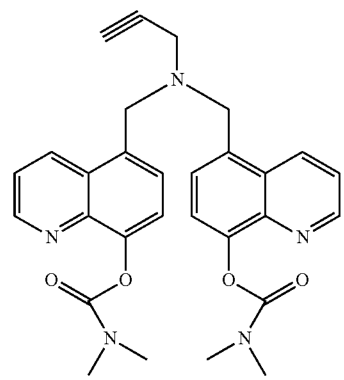 [SMILES: C#CCN(Cc1ccc(OC(=O)N(C)C)c2ncccc12)Cc1ccc(OC(=O)N(C)C)c2ncccc12] |
The invention claimed is:
1. A multifunctional compound of the formula I to VI:
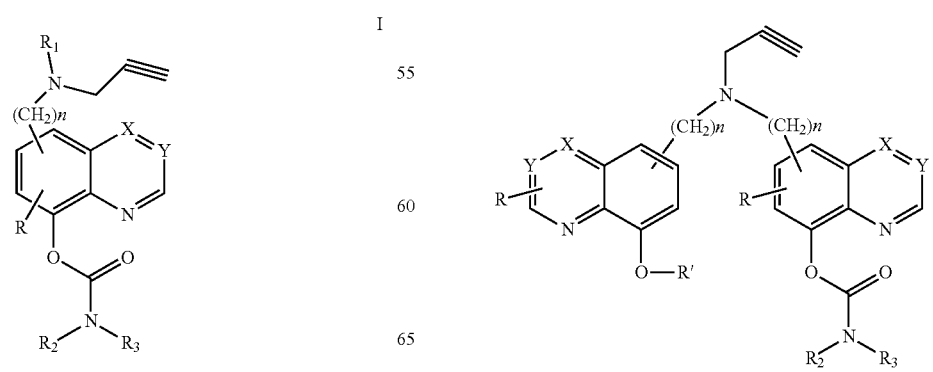

-continued

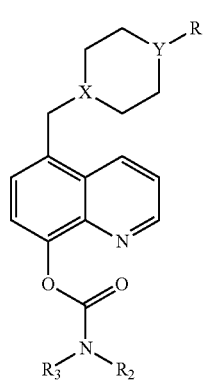
III

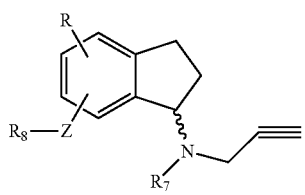
IV

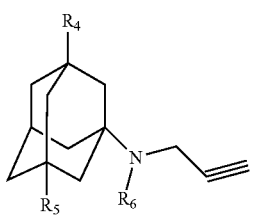
V

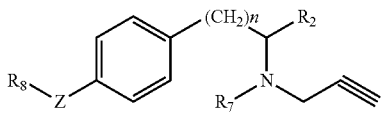
VI wherein

X, Y each independently is CH or N;

$R_1$ is H or $C_1$-$C_6$ alkyl;

R' is H or —$CONR_2R_3$

R, $R_2$, $R_3$, $R_4$, $R_5$, $R_6$ and $R_7$ each independently is H or a $C_1$-$C_{30}$ hydrocarbyl; or $R_2$ and $R_3$ together with the nitrogen atom to which they are attached form a 5-7 saturated ring optionally containing a further heteroatom selected from the group consisting of O, N and S, and optionally further substituted by an aralkyl group;

$R_8$ is CON(R)OH;

Z is $(CH_2)_m$— or O;

n is 1 to 10; and m is 0 to 10;

wherein said $C_1$-$C_{30}$ hydrocarbyl is a radical selected from the group consisting of a straight or branched alkyl, alkenyl, or alkynyl, aryl, aralkyl, cycloalkyl and arylcycloalkyl;

and an optical isomer and a pharmaceutically acceptable salt thereof.

2. The multifunctional compound of the formula I or II according to claim 1:

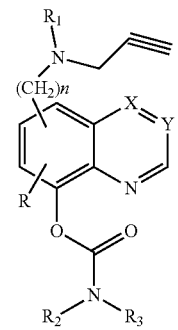
I

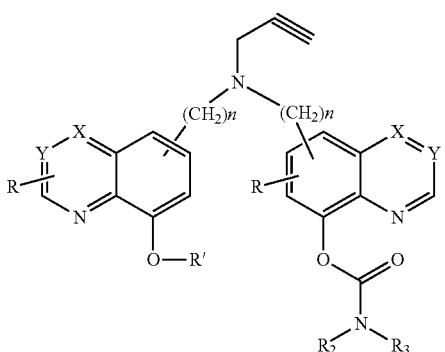
II wherein X and Y each independently is CH or N;

R is H or $C_1$-$C_{10}$ hydrocarbyl;

R' is H or —$CONR_2R_3$;

$R_1$ is H or $C_1$-$C_3$ alkyl;

$R_2$ and $R_3$ each independently is selected from the group consisting of:
(i) H;
(ii) $C_1$-$C_{10}$ alkyl;
(iii) an optionally substituted $C_3$-$C_{10}$ cycloalkyl;
(iv) an optionally substituted ($C_6$-$C_{14}$)aryl;
(v) an optionally substituted ($C_6$-$C_{14}$)aryl($C_1$-$C_6$)alkyl; and
(vi) an optionally substituted ($C_6$-$C_{14}$)aryl($C_3$-$C_6$)cycloalkyl; or $R_2$ and $R_3$ together with the nitrogen atom to which they are attached form a 5 or 6 saturated ring optionally containing a further nitrogen atom, and optionally substituted by an aralkyl; and n is 1 to 3.

3. The multifunctional compound of formula I or II according to claim 2, wherein:

X and Y each is CH;

R is H;

R' is H or —$CONR_2R_3$;

$R_1$ is H or methyl;

$R_2$ and $R_3$ each independently is selected from the group consisting of: (i) H; (ii) $C_1$-$C_6$ alkyl; (iii) adamantyl, optionally substituted by $C_1$-$C_3$ alkyl; (iv) phenyl, optionally substituted by $C_1$-$C_3$ alkyl; (v) benzyl; and (vi) an indane radical; or $R_2$ and $R_3$ together with the nitrogen atom to which they are attached form a 5 or 6 saturated ring optionally containing a further nitrogen atom, and optionally substituted by benzyl; and n is 1.

4. The multifunctional compound of the formula I according to claim 3, selected from the group consisting of the compounds herein designated compound 1, compound 2, compound 3, compound 4, compound 5, compound 6, compound 7, compound 8, compound 9, compound 10, compound 11, compound 12, compound 13, compound 14 and compound 15.

5. The multifunctional compound according to claim 3 of the formula II, selected from the compounds herein designated compound 42 or compound 43.

6. The multifunctional compound of the formula III according to claim 1:

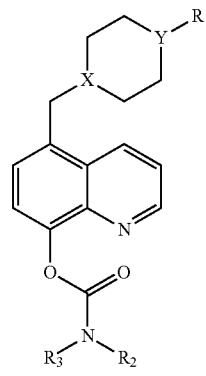

III wherein
X, Y each independently is CH or N;
R is a $C_3$-$C_6$ alkynyl; and
$R_2$ and $R_3$ each independently is selected from the group consisting of:
(i) H;
(ii) $C_1$-$C_{10}$ alkyl;
(iii) an optionally substituted $C_3$-$C_{10}$ cycloalkyl;
(iv) an optionally substituted ($C_6$-$C_{14}$)aryl;
(v) an optionally substituted ($C_6$-$C_{14}$)aryl($C_1$-$C_6$)alkyl; and
(vi) an optionally substituted ($C_6$-$C_{14}$)aryl($C_3$-$C_6$)cycloalkyl; or
$R_2$ and $R_3$ together with the nitrogen atom to which they are attached form a 5 or 6 saturated ring optionally containing a further nitrogen atom, and optionally substituted by an aralkyl.

7. The multifunctional compound of the formula III according to claim 6, wherein: X and Y each independently is CH or N; R is a propargyl group; and $R_2$ and $R_3$ each independently is H or $C_1$-$C_3$ alkyl; or $R_2$ and $R_3$ together with the nitrogen atom to which they are attached form a 5 or 6 saturated ring optionally containing a further nitrogen atom, and optionally substituted by benzyl.

8. The multifunctional compound of the formula III according to claim 7, selected from the group consisting of the compounds herein designated compound 16, compound 17, compound 18, compound 19, compound 20, compound 21, compound 22 and compound 23.

9. The multifunctional compound of the formula IV according to claim 1:

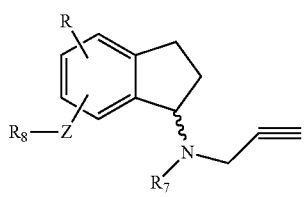

IV wherein
R and $R_7$ each independently is H or $C_1$-$C_{10}$ hydrocarbyl;
$R_8$ is —CON(R)OH;
Z is O or —$(CH_2)_m$—; and m is 0 to 3.

10. The multifunctional compound of the formula IV according to claim 9, wherein: R is H; $R_7$ is H or $C_1$-$C_3$ alkyl; $R_8$ is —CONHOH; Z is O or —$(CH_2)_m$—; and m is 0.

11. The multifunctional compound of the formula IV according to claim 10, selected from the group consisting of the compounds herein designated compound 24, compound 25, compound 26, compound 27, compound 28, compound 29, compound 30 and compound 31.

12. The multifunctional compound of the formula. V according to claim 1:

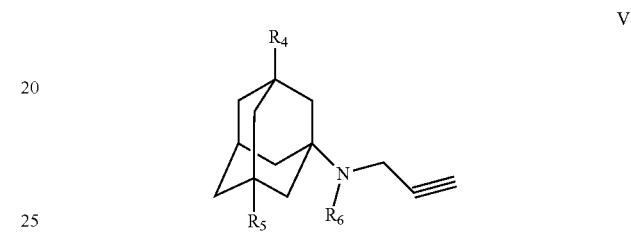

V wherein $R_4$, $R_5$ and $R_6$ each independently is H or $C_1$-$C_{10}$ hydrocarbyl.

13. The multifunctional compound of the formula V according to claim 12, wherein $R_4$ and $R_5$ is each H or a $C_1$-$C_6$ alkyl and $R_6$ is H, $C_1$-$C_6$ alkyl or $C_2$-$C_6$ alkynyl.

14. The multifunctional compound of the formula V according to claim 13, selected from the group consisting of the compounds herein designated compound 36, compound 37, compound 38, compound 39, compound 40, and compound 41.

15. The multifunctional compound of the formula VI according to claim 1:

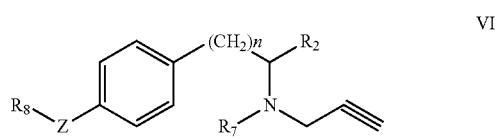

VI wherein
$R_2$ and $R_7$ each independently is H or $C_1$-$C_{10}$ hydrocarbyl;
$R_8$ is —CON(R)OH;
Z is O or —$(CH_2)_m$—;
R is H or $C_1$-$C_{10}$ hydrocarbyl;
m is 0 to 6; and n is 1 to 6.

16. The multifunctional compound of the formula. VI according to claim 15, wherein $R_2$ and $R_7$ each independently is H or a $C_1$-$C_6$ alkyl; $R_8$ is —CONHOH; Z is O or —$(CH_2)_m$—; m is 0; and n is 1.

17. The multifunctional compound of the formula VI according to claim 16, selected from the group consisting of the compounds herein designated compound 32, compound 33, compound 34 and compound 35.

18. A pharmaceutical composition comprising a multifunctional compound according to claim 1 and a pharmaceutically acceptable carrier.

* * * * *